US006875790B2

(12) United States Patent
Bertenshaw et al.

(10) Patent No.: US 6,875,790 B2
(45) Date of Patent: Apr. 5, 2005

(54) CYCLIC SULFONE CONTAINING RETROVIRAL PROTEASE INHIBITORS

(75) Inventors: Deborah E. Bertenshaw, Brentwood, MO (US); Daniel Getman, Chesterfield, MO (US); Robert M. Heintz, Ballwin, MO (US); John J. Talley, St. Louis, MO (US); Kathryn L. Reed, Raleigh, NC (US); Robert Alan Chrusciel, Portage, MI (US); Michael Clare, Skokie, IL (US)

(73) Assignees: G. D. Searle & Co., Skokie, IL (US); Pharmacia Corporation (Monsanto Corporation), St. Louis, MO (US)

( * ) Notice: Subject to any disclaimer, the term of this patent is extended or adjusted under 35 U.S.C. 154(b) by 0 days.

(21) Appl. No.: 10/369,197

(22) Filed: Feb. 20, 2003

(65) Prior Publication Data

US 2004/0010143 A1 Jan. 15, 2004

Related U.S. Application Data

(60) Continuation of application No. 09/973,991, filed on Oct. 11, 2001, now Pat. No. 6,552,203, which is a continuation of application No. 09/870,748, filed on Jun. 1, 2001, now Pat. No. 6,329,524, which is a division of application No. 09/177,100, filed on Oct. 22, 1998, now Pat. No. 6,265,583, which is a division of application No. 08/556,883, filed on Nov. 2, 1995, now Pat. No. 5,849,784, which is a division of application No. 07/998,187, filed on Dec. 29, 1992, now Pat. No. 5,514,801.

(51) Int. Cl.$^7$ ...................... A61K 31/38; A61K 31/335; C07D 215/16; C07D 337/00; C07D 335/02
(52) U.S. Cl. ...................... 514/431; 514/432; 514/445; 514/446; 514/448; 549/9; 549/13; 549/28; 549/72; 546/156
(58) Field of Search ................................. 514/431, 432, 514/445, 446, 448; 549/9, 13, 28, 72; 546/156

(56) References Cited

U.S. PATENT DOCUMENTS

| 4,450,164 | A |   | 5/1984  | Bristol et al. |
|-----------|---|---|---------|----------------|
| 4,477,441 | A |   | 10/1984 | Boger et al. |
| 4,514,391 | A |   | 4/1985  | Gordon et al. |
| 4,548,926 | A |   | 10/1985 | Matsueda et al. |
| 4,599,198 | A |   | 7/1986  | Hoover |
| 4,616,088 | A |   | 10/1986 | Ryono et al. |
| 4,668,769 | A |   | 5/1987  | Hoover |
| 4,668,770 | A |   | 5/1987  | Boger et al. |
| 4,757,050 | A |   | 7/1988  | Natarajan et al. |
| 4,857,507 | A |   | 8/1989  | Rosenberg et al. |
| 4,880,938 | A |   | 11/1989 | Freidinger |
| H725      | H |   | 1/1990  | Gordon |
| 4,963,530 | A |   | 10/1990 | Hemmi et al. |
| 4,977,277 | A |   | 12/1990 | Rosenberg et al. |
| 5,484,926 | A |   | 1/1996  | Dressman |
| 5,514,801 | A | * | 5/1996  | Bertenshaw et al. ........ 546/146 |
| 5,824,688 | A |   | 10/1998 | Kalish |
| 5,827,858 | A |   | 10/1998 | Kalish |
| 5,827,859 | A |   | 10/1998 | Kalish |
| 5,827,891 | A |   | 10/1998 | Kalish |
| 5,849,784 | A | * | 12/1998 | Bertenshaw et al. ........ 514/432 |
| 6,265,583 | B1 | * | 7/2001 | Bertenshaw et al. ........ 548/127 |
| 6,552,203 | B2 | * | 4/2003 | Bertenshaw et al. ........... 549/9 |

FOREIGN PATENT DOCUMENTS

| AU | 79823/87     | 4/1988  |
|----|--------------|---------|
| EP | 0114993      | 8/1984  |
| EP | 172347       | 2/1986  |
| EP | 223437       | 5/1987  |
| EP | 0264795      | 4/1988  |
| EP | 0104041      | 7/1988  |
| EP | 337714       | 10/1989 |
| EP | 0342541      | 11/1989 |
| EP | 0346847      | 12/1989 |
| EP | 356223       | 2/1990  |
| EP | 289898 A3    | 10/1990 |
| EP | 389898 A2    | 10/1990 |
| EP | 393445       | 10/1990 |
| EP | 393457       | 10/1990 |
| EP | 402646       | 12/1990 |
| GB | 2184730      | 7/1987  |
| GB | 2200115      | 7/1988  |
| GB | 2209752      | 5/1989  |
| WO | WO 84/03044  | 8/1984  |
| WO | WO 92/00750  | 1/1992  |

OTHER PUBLICATIONS

Roberts et al., "Rational Design of Peptide–Based Proteinase Inhibitors", *Science*, 248, 358 (1990).
Erickson et al., "Design Activity and 2.8A Crystal Structure of $C_2$ Symmetric Inhibitor Complexed to HIV–1 Protease", *Science*, 249, 527 (1990).
Pearl et al., "Sequence specificity of Retroviral Protease", *Nature*, vol. 328, No. 6130, Aug. 6–12, 1987, p. 482.
Martin, Drugs of the Future, 1991 16(3), 210–212.
Meek et al., "Inhibition of HIV–1 Protease in Infected T–lymphocytes by Synthetic Peptide Analogues", *Nature*, 343, 90 (1990.
McQuade et al., "A Synthetic HIV–1 Protease Inhibitor with Antiviral Activity Arrests HIV–Like Particle Maturation", *Science*, 274, 454–456 (1990).
D.H. Rich and V.J. Hunby; Dept. Struct. Funct. Proc. Am. Peptide Inhibitors of Protease Sym. $8^{th}$ ed., pp. 511–520 (1983).
Rosenberg et al., *J. Med. Chem.*, 30, 1224–1228 (1987).
U.S. patent application Ser. No. 07/789,646 by John J. Talley et al., filed Nov. 14, 1991, entitled "Retroviral Protease Inhibitors" (07–21(807)A).

(Continued)

Primary Examiner—D. Margaret Seaman
(74) Attorney, Agent, or Firm—Banner & Witcoff, Ltd.

(57) ABSTRACT

The present invention relates to cyclic sulfone moiety-containing hydroxyethylamine protease inhibitor compounds and pharmaceutical or method of use therefor, particularly as an inhibitor of HIV protease.

20 Claims, No Drawings

OTHER PUBLICATIONS

U.S. patent application Ser. No. 07/789,645 by John J. Talley et al., filed Nov. 14, 1991, entitled "Retroviral Protease Inhibitors" (07–21(829)A).

U.S. patent application Ser. No. 07/789,644 by John J. Talley et al., filed Nov. 14, 1991, entitled "Retroviral Protease Inhibitors" (07–21(831)A).

U.S. patent application Ser. No. 07/789,642 by John J. Talley et al., filed Nov. 14, 1991, entitled "Retroviral Protease Inhibitors" (07–21(827)A).

U.S. patent application Ser. No. 07/789,643 by John J. Talley et al., filed Nov. 14, 1991, entitled "Retroviral Protease Inhibitors" (07–21(830)A).

U.S. patent application Ser. No. 07/886,556 by John J. Talley et al., filed May 20, 1992, entitled "Retroviral Protease Inhibitors" (2–2709/1).

U.S. patent application Ser. No. 07/886,663 by John J. Talley et al., filed May 20, 1992, entitled "Retroviral Protease Inhibitors" (2–2710/1).

U.S. patent application Ser. No. 07/886,531 by John J. Talley et al., filed May 20, 1992, entitled "Retroviral Protease Inhibitors" (2–2711/1).

U.S. patent application Ser. No. 07/886,547 by John J. Talley et al., filed May 20, 1992, entitled "Retroviral Protease Inhibitors" (2–2712/1).

U.S. patent application Ser. No. 07/886,700 by John J. Talley et al., filed May 20, 1992, entitled "Retroviral Protease Inhibitors" (07–21(879A).

U.S. patent application Ser. No. 07/935,071 by Michael Vazquez et al., filed Aug. 25, 1992, entitled Sulfonylakanoy-lamino Hydroxyethylamino Sulfonamides Useful as Retroviral Protease Inhibitors (C–2703).

U.S. patent application Ser. No. 07/935,490 by Michael Vazquez et al., filed Aug. 25, 1992, entitled Succinoylamino Hydroxyethylamino Sulfonamides Useful as Retroviral Protease Inhibitors (C–2704).

U.S. patent application Ser. No. 07/934,984 by Michael Vazquez et al., filed Aug. 25, 1992, entitled $\alpha$– and $\beta$–amino Acid Hydroxyethylamino Sulfonamides Useful as Retroviral Protease Inhibitors (C–2705).

U.S. patent application Ser. No. 07/969,683 by Michael Vazquez et al., filed Oct. 30, 1992, entitled Succinolyamino Hydroxyethylamino Sulfamic Acids Useful as Retroviral Protease Inhibitors (C–2741).

U.S. patent application Ser. No. 07/969,612 by Michael Vazquez et al., filed Oct. 30, 1992, entitled Sulfonylakanoy-lamino Hydroxyethylamino Sulfamic Acids Useful Acids Useful as Retroviral Protease Inhibitors (C–2742).

U.S. patent application Ser. No. 07/968,712 by Michael Vazquez et al., filed Oct. 30, 1992, entitled $\alpha$– $\beta$–Amino Acid Hydroxyethylamino Sulfony Urea Derivatives Useful as Retroviral Protease Inhibitors (C–2751).

U.S. patent application Ser. No. 07/969,616 by Michael Vazquez et al., filed Oct. 30, 1992, entitled Sulfonylalkanoy-lamino Hydroxyethylamino Sulfonyl Urea Derivatives Useful as Retroviral Protease Inhibitors (C–2752).

U.S. patent application Ser. No. 07/969,682 by Michael Vazquez et al., filed Oct. 30, 1992, entitled Succinolyamino Hydroxyethylamino Sulfonyl Urea Derivatives Useful as Retroviral Protease Inhibitors (C–2753).

U.S. patent application Ser. No. 07/968,730 by Michael Vazquez et al., filed Oct. 30, 1992, entitled $\alpha$– $\beta$–Amino Acid Hydroxyethylamino Sulfamic Acid Derivatives Useful as Retroviral Protease Inhibitors (C–2740).

\* cited by examiner

CYCLIC SULFONE CONTAINING RETROVIRAL PROTEASE INHIBITORS

CROSS REFERENCE TO RELATED APPLICATIONS

This application is a continuation of U.S. patent application Ser. No. 09/973,991, filed Oct. 11, 2001, now U.S. Pat. No. 6.552.203, which is a continuation of U.S. patent application Ser. No. 09/870,748, filed Jun. 1, 2001, now U.S. Pat. No. 6,329,524, which is a divisional of U.S. patent application Ser. No. 09/177,100, filed Oct. 22, 1998, now U.S. Pat. No. 6,265,583, which is a divisional of U.S. patent application Ser. No. 08/556,883, filed Nov. 2, 1995, now U.S. Pat. No. 5,849,784, which is a divisional of U.S. patent application Ser. No. 07/998,187, filed Dec. 29, 1992, now U.S. Pat. No. 5,514,801, each incorporated herein by reference in its entirety.

BACKGROUND OF THE INVENTION

1. Field of the Invention

The present invention relates to retroviral protease inhibitors and, more particularly relates to novel compounds and a composition and method for inhibiting retroviral proteases. This invention, in particular, relates to cyclic sulfone moiety-containing hydroxyethylamine protease inhibitor compounds, a composition and method for inhibiting retroviral proteases such as human immunodeficiency virus infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit replication of structural proteins and, more importantly, the retroviral protease itself. In this manner, retroviral proteases can be effectively inhibited.

Several classes of mimetic compounds are known to be useful as inhibitors of the proteolytic enzyme renin. See, for example, U.S. Pat. No. 4,599,198; G.B. 2,184,730; G.B. 2,209,752; EPO 264 795; G.B. 2,200,115 and U.S. SIR H725; and U.S. Pat. No. 4,599,198 disclose urea-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

Several classes of mimetic compounds have been proposed, particularly for inhibition of proteases, such as for inhibition of HIV protease. Such mimetics include hydroxyethylamine isoteres and reduced amide isosteres. See, for example, EPO 346 847; EPO 342,541; Roberts et al, "Rational Design of Peptide-Bases Proteinase Inhibitors", *Science*, 248, 358 (1990); and Erickson et al, "Design Activity, and 2.8 Å Crystal Structure of a $C_2$ Symmetric Inhibitor Complexed to HIV-1 Protease", *Science*, 249, 527 (1990). EPO 346 847 discloses certain N-heterocyclic moiety-containing hydroxyethylamine protease inhibitor compounds, but does not suggest or disclose those of the present invention.

Dipeptide isosteres as inhibitors of HIV protease are found in EP application numbers 91309292, 91309028.8 and 91309302.7.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as cyclic sulfone- and either urea- or N-heterocyclic moiety-containing hydroxyethylamine inhibitor compounds.

DETAILED DESCRIPTION OF THE INVENTION

In accordance with the present invention, there are provided novel retroviral protease inhibiting compounds or a pharmaceutically acceptable salt, prodrug or ester thereof.

Generally, the present invention is a compound of the formula (I")

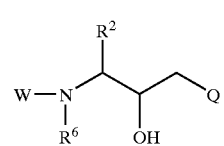

and a pharmaceutically acceptable salt, prodrug or ester thereof; wherein Q, $R^2$ and $R^6$ are as defined below and W represents (a)

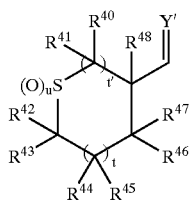

or (b)

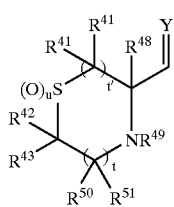

wherein Y' is as defined below; and t represents 0, 1 and 2, preferably 1;

t' represents 1 and 2, preferably 1;

u represents 0, 1 and 2;

$R^{40}$, $R^{41}$, $R^{42}$, $R^{43}$, $R^{48}$, $R^{49}$, $R^{50}$ and $R^{51}$ independently represent hydrogen and alkyl;

$R^{44}$, $R^{45}$, $R^{46}$, $R^{47}$ and independently represent hydrogen, alkyl and hydroxy; or one of (a) $R^{40}$ together with $R^{48}$, (b) $R^{43}$ together with $R^{45}$, (c) $R^{45}$ together with $R^{47}$, and (d) $R^{47}$ together with $R^{48}$ represent a bond; or one of (a) $R^{44}$ together with $R^{45}$, (b) $R^{46}$ together with $R^{47}$ or (c) $R^{50}$ together with $R^{51}$ represent a double bond oxygen.

$R^{40}$ through $R^{48}$ most preferably represent hydrogen, however, both $R^{46}$ and $R^{47}$ also preferably represent methyl at the same time $R^{40}$ through $R^{45}$ and $R^{48}$ are all hydrogen. Additionally, $R^{48}$ is preferably hydrogen and the stereo configuration of the carbon to which $R^{48}$ is attached is preferably in the configuration represented by the upper spot in Example 4 set forth hereinafter, and preferably wherein the stereochemistry about the hydroxy group may be designated as (R).

Thus, the present invention compound is preferably of the formula (I')

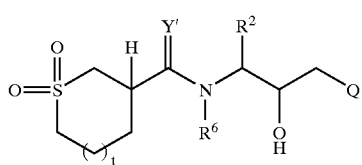

I' or a pharmaceutically acceptable salt, prodrug or ester thereof; and wherein Q is:

(1)

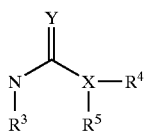

-continued (2)

(3)

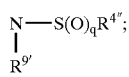

(4)

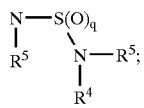

(5)

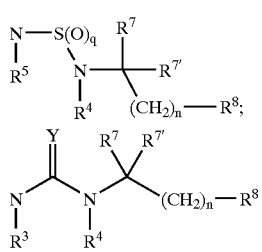

and wherein t, Y', $R^6$, $R^2$, Y, $R^3$, X, $R^4$, $R^5$, $R^{4'}$ and $R^{5'}$ are as defined below, q represents 1 or 2;

$R^{4''}$, $R^9$ and $R^{9'}$ independently represent radicals as defined by $R^3$;

n represents 0 to 6;

$R^7$ and $R^{7'}$ independently represent radicals as defined for $R^3$ and amino acid side chains selected from the group consisting of valine, isoleucine, glycine, alanine, alloisoleucine, asparagine, leucine, glutamine, and t-butylglycine or $R^7$ and $R^{7'}$ together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas $C(O)R^{16}$, $CO_2R^{16}$, $SO_2R^{16}$, $SR^{16}$, $CONR^{16}R^{17}$, $CF_3$ and $NR^{16}R^{17}$;

wherein $R^{16}$ and $R^{17}$ independently represent hydrogen and radicals as defined for $R^3$, or $R^{16}$ and $R^{17}$ together with a nitrogen to which they are attached in the formula $NR^{16}R^{17}$ represent heterocycloalkyl and heteroaryl radicals.

A more preferred class of retroviral inhibitor compounds of the present invention are those represented by the formula (I)

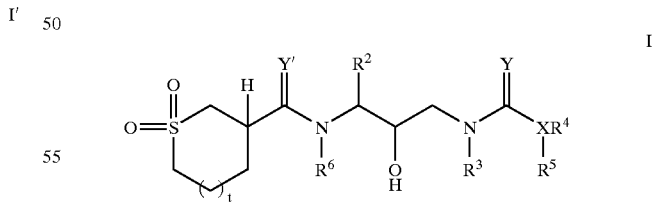

I or a pharmaceutically acceptable salt, prodrug or ester thereof, and wherein:

t represents either 0, 1 or 2;

$R^2$ represents alkyl, aryl, cycloalkyl, cycloalkylalkyl, and aralkyl radicals, which radicals are optionally substituted with a substituent selected from the group consisting of alkyl and halogen radicals, $-NO_2$, $-CN$, $-CF_3$, $-OR_9$, $-SR^9$, wherein $R^9$ represents hydrogen and alkyl radicals;

R³ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl; heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, thioalkyl, alkylthioalkyl, and arylthioalkyl radicals and the sulfone or sulfoxide derivatives thereof;

Y and Y' independently represent O, S and $NR^{15}$ wherein $R^{15}$ represents hydrogen and radicals as defined for $R^3$;

X represents N, CH or O;

$R^4$ and $R^5$ independently represent hydrogen and radicals as defined by $R^3$, or when X represents N, $R^4$ and $R^5$ together with the nitrogen atom to which they are bonded represent heterocycloalkyl and heteroaryl radicals, or when X represents CH, $R^4$ and $R^5$ together with the carbon atom to which they are bonded represent a cycloalkyl radical with the proviso $R^5$ is nothing when X is O;

$R^6$ represents hydrogen and alkyl radicals;

The compound of the formula I preferably includes a compound wherein Y and Y' represent O, $R^6$ represents hydrogen, t represents 1 and X represents N.

Another compound of the formula I preferably includes a compound wherein $R^2$ represents benzyl, cyclohexylmethyl, n-butyl, 2-naphthylmethyl, p-fluorobenzyl and isobutyl.

Another compound of the formula I preferably includes a compound wherein $R^4$ and $R^5$ independently represent hydrogen, methyl, ethyl, isopropyl and tertiary-butyl.

Another compound of the formula I preferably includes a compound wherein $R^4$ and $R^5$ together with the nitrogen to which they are attached represent a 5 to 8 membered heterocycloalkyl ring.

And finally, another compound of the formula I preferably includes a compound wherein $R^3$ is isobutyl, n-butyl, isoamyl, benzyl, p-fluorobenzyl and cyclohexylmethyl.

Another more preferred class of retroviral inhibitor compounds of the present invention are those represented by the formula (II)

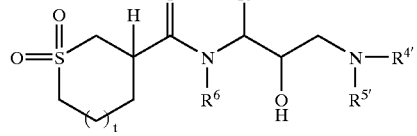

or a pharmaceutically acceptable salt, prodrug or ester thereof, and wherein:

t, $R^2$, Y', and $R^6$ represent radicals as defined above; and $R^{4'}$ and $R^{5'}$ together with the nitrogen atom to which they are bonded represent an N-heterocyclic moiety.

A compound of the formula II preferably includes a compound wherein Y' represents O, t represents 1 and $R^6$ represents hydrogen.

Another compound of the formula II preferably includes a compound wherein R represents benzyl, p-fluorobenzyl, cyclohexylmethyl, 2-naphthylmethyl, n-butyl and isobutyl.

Another compound of the formula II preferably includes a compound wherein $NR^{4'}R^{5'}$ represents 2-[[(1,1-dimethylethyl)amino]carbonyl]decahydroisoquinolinyl- or 2-[[(1,1-dimethylethyl)amino]carbenyl]piperidinyl.

Another more preferred class of retroviral inhibitor compounds of the present invention are those represented by the formula (III)

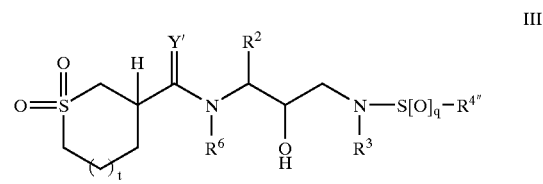

or a pharmaceutically acceptable salt, prodrug or ester thereof, and wherein t, Y', $R^6$, $R^2$ and $R^3$ represent radicals as defined above; and q represents 1 or 2; and $R^{4''}$ represents radicals as independently defined by $R^3$.

A compound of the formula III preferably includes a compound wherein Y' represents O, t represents 1, $R^6$ represents hydrogen and q represents 2.

Another compound of the formula III preferably includes a compound wherein $R^2$ represents benzyl, p-fluorobenzyl, 2-naphthylmethyl, cyclohexylmethyl, n-butyl and isobutyl.

Another compound of the formula III preferably includes a compound wherein $R^3$ represents isobutyl, n-propyl, n-butyl, isoamyl, cyclohexylmethyl and cyclohexyl.

Another compound of the formula III preferably includes a compound wherein $R^{4''}$ represents an aryl or heteroaryl radical.

Another compound of the formula III preferably includes a compound wherein $R^{4''}$ represents a para-substituted phenyl wherein the substituent is hydrogen, fluoro, chloro, bromo, nitro, hydroxy, methoxy and amino.

Other more preferred classes are as follows:

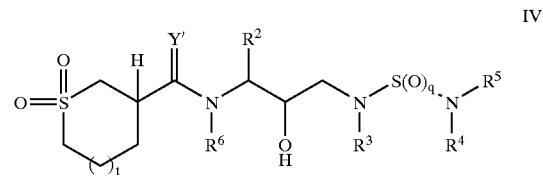

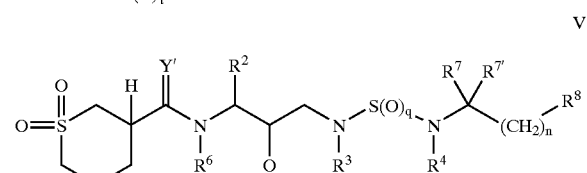

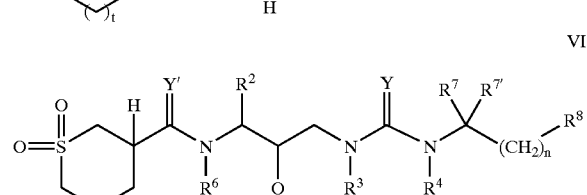

or a pharmaceutically acceptable salt, prodrug or ester thereof;

wherein t, Y', $R^6$, $R^2$, $R^3$, Y, q, $R^4$, $R^5$, $R^7$, $R^{7'}$, n and $R^8$ are as defined above.

A compound of the formula IV preferably includes a compound wherein Y' represents O, $R^6$ represents hydrogen and q represents 2.

Another compound of the formula IV preferably includes a compound wherein $R^2$ represents benzyl, p-fluorobenzyl, 2-naphthylmethyl, n-butyl, cyclohexylmethyl and isobutyl.

Another compound of the formula IV preferably includes a compound wherein $R^3$ represents isobutyl, n-propyl, n-butyl, isoamyl, cyclohexylmethyl and cyclohexyl.

Another compound of the formula IV preferably includes a compound wherein $R^4$ and $R^5$ independently represent hydrogen, methyl, ethyl, isopropyl, t-butyl, phenyl and cyclohexyl or wherein $R^4$ and $R^5$ and the nitrogen to which they are attached represent a 5 to 8 membered heterocycloalkyl ring.

A compound of the formula V preferably includes a compound wherein Y' represents O, $R^6$ represents hydrogen, t represents 1, and q represents 2.

Another compound of the formula V preferably includes a compound wherein $R^2$ represents benzyl, p-fluorobenzyl, 2-naphthylmethyl, cyclohexylmethyl, n-butyl, and iso-butyl.

Another compound of the formula V preferably includes a compound wherein $R^3$ represents isobutyl, n-propyl, n-butyl, isoamyl, cyclohexylmethyl and cyclohexyl.

A compound of the formula VI preferably includes a compound wherein Y and Y' both represent O, $R^6$ represents hydrogen and t represents 1.

Another compound of the formula VI preferably includes a compound wherein $R^2$ represents benzyl, p-fluorobenzyl, 2-naphthylmethyl, cyclohexylmethyl, n-butyl, and isobutyl.

Another compound of the formula VI preferably includes a compound wherein $R^3$ represents isobutyl, n-propyl, isoamyl, n-butyl, cyclohexylmethyl, benzyl, p-fleorobenzyl and p-methoxybenzyl.

Another compound of the formula VI preferably includes a compound wherein $R^7$ and $R^{7'}$ independentyly represent hydrogen, methyl and ethyl, or together with the carbon to which they are attached represent a 3 to 6 membered cycloalkyl ring.

The most preferred compounds of the present invention are those of the formula I through VI wherein t is 1, $R^6$ is hydrogen, and $R^2$ is an aralkyl, alkyl or cycloalkylalkyl radical.

Each of the compounds of the present invention is represented by formula having at least three optically active carbon centers. The present invention is meant to include compounds having each of the combinations of optical rotation and mixtures thereof. The present compounds may have additional stereoisomers and thus is also meant to include each of such isomers.

In each of the Formula I, II, III, IV, V, and VI a preferred structure is one where stereo configuration of the group —C(OH)— shown by the OH on the carbon adjacent the carbon having $R^2$ attached is represented by the stereochemistry designated as (R).

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, n-butyl, isobutyl, sec-butyl, tert-butyl, pentyl, isoamyl, hexyl, octyl and the like. The term "thioalkyl" means aralkyl radical having at least one sulfur atom, wherein alkyl has the significance given above. An example of athioalkyl is —$C(CH_3)_2SCH_3$. The corresponding sulfoxide and sulfone of this thioalkyl are —$C(CH_3)_2S(O)CH_3$ and —$C(CH_3)_2S(O)_2CH_2$, respectively. The term "alkenyl", alone or in combination, means a straight-chain or branched-chain hydrocarbon radical having one or more double bonds and containing from 2 to about 18 carbon atoms preferably from 2 to about 8 carbon atoms. Examples of suitable alkenyl radicals include ethenyl, propenyl, alyl, 1,4-butadienyl and the like. The term "alkynyl", alone or in combination, mans a straight-chain hydrocarbon radical having one or more triple bonds and containing from 2 to about 10 carbon atoms. Examples of alkynl radicals include ethynyl, propynyl (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like. The term "cycloalkylalkyl" means an alkyl radical as defined above which is substituted by a cycloalkyl radical containing from about 3 to about 8, preferably from about 3 to about 6, carbon atoms. The term "aryl", alone or in combination, means a phenyl or naphthyl radical which optionally carries one or more substituents selected from alkyl, alkoxy, halogen, hydroxy, amino, nitro and the like, such as phenyl, p-tolyl, 4-hydroxyphenyl, 1-naphthyl, 2-naphthyl, and the like. The term "aralkyl", alone or in combination, means an alkyl radical as defined above in which one hydrogen atom is benzyl, 2-phenylethyl and the like. The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl. The term "aryloxy", alone or in combination, means a radical of the formula aryl-O— in which the term "aryl" has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-chlorohydrocinnamoyl, 4-aminohydrocinnamoyl, 4-phenylbutyryl, (1-naphthyl)acetyl, derived from a monocylic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclylalkyl group or the like is a saturated or partially unsaturated monocyclic, bicyclic or tricyclic heteroycle which contains one or more hetero atoms selected from nitrogen, oxygen and sulphur, which is optionally substituted on one or more carbon atoms by halogen alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. The heteroaryl portion of a heteroaroyl, heteroaryloxycarbonyl, or heteroaralkoxycarbonyl group or the like is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol-4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl (e.g., 2-quinolinyl, 3-quinolinyl, 1-oxido-2-quinolinyl, etc.), isoquinolinyl (e.g., 1-isoquinolinyl, 3-isoquinolinyl, etc.), tetra hydroquinolinyl (e.g., 1,2,3,4-tetrahydro-1-oxoisoquinolinyl, etc), quinoxalinyl, beta-carbolinyl, 2-benzofurancarbonyl, 1-, 2-,4-, or 5-benzimidazolyl, and the like. The term "cycloalkylalkoxycarbonyl" means an acyl group derived from a cycloalkylalkoxycarboxylic acid of the formula cycloalkylalkyl-O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclylalkanoyl" is an acyl radical derived from a heterocyclyl-substituted alkane carboxylic acid wherein heterocyclyl has the significance given above. The term "heterocyclyloxycarbonyl" means an acyl group derived from heterocyclyl-O—COOH wherein heterocyclyl is as defined above. The term "heterocyclylalkanoyl" means an acyl radical of the formula aryl-O-alkanoyl wherein aryl and alkanoyl have the significance given above. The term "heterocyclylalkoxycarbonyl" means an acyl radical derived from heterocyclyl-substituted alkane-O—COOH wherein heterocyclyl has the significance given above. The term "heteroaryloxycarbonyl" means an acylradical derived from a carboxylic acid represented by heteroaryl-O—COOH wherein heteroaryl has the significance given above.

The term "aminocarbonyl" alone or in combination, means an amino-substituted carbonyl(carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like. The term "aminoalkanoyl" means an acyl radical-derived from an amino substituted alkanecarboxylic acid wherein the amino group can be a primary, secondary or tertiary amino group containing substituents selected from the group consisting of hydrogen, cycloalkyl, cycloalkylalkyl radicals and the like, examples of which include N,N-dimethylaminoacetyl and N-benzylaminoacetyl. The term "halogen" means fluorine, chlorine, bromine or iodine. The term "leaving group" generally refers to groups readily displaceable by a nucleophile, such as an amine, a thiol or an alcohol nucleophile. Such leaving groups are well known and include carboxylates, N-hydroxysuccinimide, N-hydroxybenzotriazole, halides, triflates, tosylates, —OR and —SR and the like. Preferred leaving groups are indicated herein where appropriate. The term "N-heterocyclic moiety" is a heterocyclic radical with a nitrogen radical bond site which may be a heterocycloalkyl or heteroaryl, wherein heterocycloalkyl and heteroaryl have the significance given above, with the addition that polycyclic heteroaryl may be fully aromatic or partially aromatic, for example, a fused heterocycloalkylaryl and a fused heteroarylcycloalkyl, and heterocycloalkyl and cycloalkyl may also be bridged. Preferably, the N-heterocyclic moiety has 5, 6 or 7 members when monocyclic; 5, 6 or 7 members in a ring with 1, 2 or 3 members in a bridge when a bridged monocyclic; 11, 12 or 13 members when bicyclic; and 11 to 16 members when tricyclic.

Examples of N-heterocyclic moieties include, but are not limited to, those represented by the following formulas:

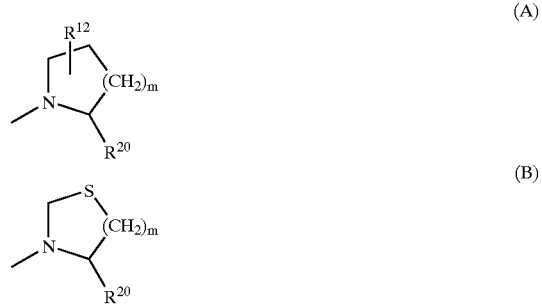

wherein:

R²⁰ represents hydrogen, alkyl, alkoxycarbonyl, monoalkylcarbamoyl, monoaralkylcarbamoyl, monoarylcarbamoyl or a group of the formula:

wherein:

R¹⁰ and R¹¹ each represents alkyl;

R¹² represents hydrogen, hydroxy, alkoxycarbonylamino or acylamino;

R¹³ represents hydrogen, alkyl, aryl, alkoxycarbonyl or acyl;

m is 1, 2, 3, or 4;

p is 1 or 2; and r is independently 0, 1 or 2.

Procedures for preparing the compounds of Formulas I, II, III, IV, V and VI are set forth below. It should be noted that the general procedure is shown as it relates to preparation of compounds having the specified stereochemistry, for example, wherein the stereochemistry about the hydroxy group is designated as (R). However, such procedures are generally applicable to those compounds of opposite configuration, e.g., where the stereochemistry about the hydroxyl group is (S). The terms (R) and (S) configuration are as defined by the IUPAC 1974 Recommendations for Section E, Fundamental Stereochemistry, Pure appl. Chem. (1976) 45, 13–30.

Likewise, procedures to obtain the preferred stereochemistry and its opposite configuration for the carbon to which R⁴⁸ is attached, and particularly when R⁴⁸ is hydrogen, are generally applicable from that disclosed in Example 4 below.

Preparation of Compounds of Formula I, III, IV, V and VI

Preparation of the compounds of Formula I are accomplished by preparing a cyclic sulfone carboxylic acid according to the following Scheme 1 and Scheme 1a:

Scheme 1

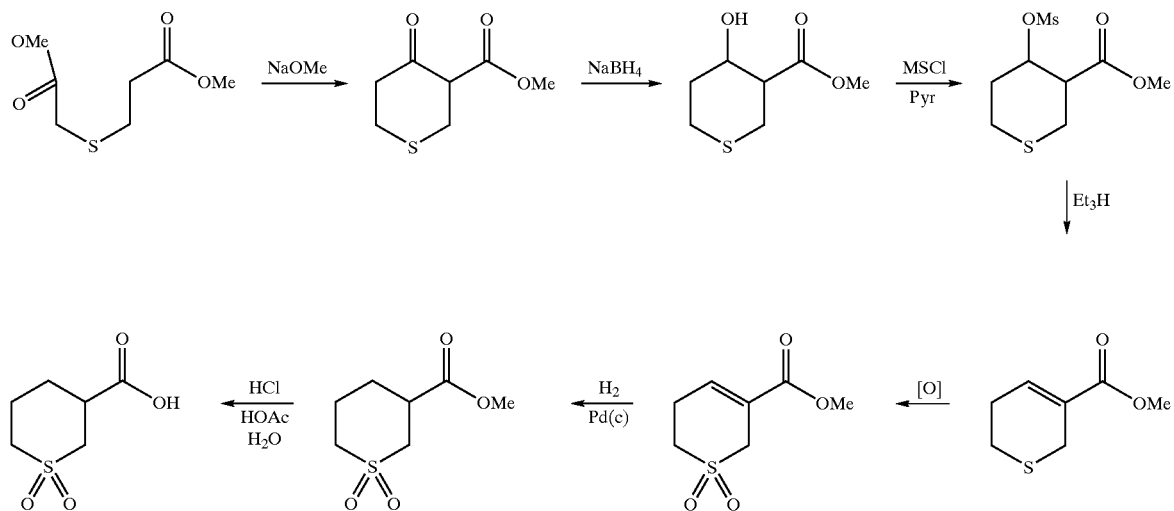

Exemplary conditions for the preparation of Scheme 1 are found in Preparation 1 hereinafter. For a cyclic sulfone having a seven membered ring the corresponding starting material may be substituted using analogous reaction conditions. On the other hand, for a cyclic sulfone having a five membered ring, the known starting material, 3-methoxycarbonyl-2,5-dihydrothiophene-1,1-dioxide is hydrogenated and deesterified in a manner analogous to the last two steps shown in Scheme 1 and exemplified in Preparation 2 hereinafter.

A urea isostere of the formula A, the formula B, or the formula C that is prepared according to the methods of PCT Number WO-PCT/US92/8613 or PCT Application Number PCT/US92/08700, and PCT/US91/8593, respectively, which are incorporated by reference therefor, is then coupled with the cyclic sulfone carboxylic acid prepared above to obtain the compound of the formula I or VI in the manner set out in Scheme 2 hereinafter:

Scheme 2

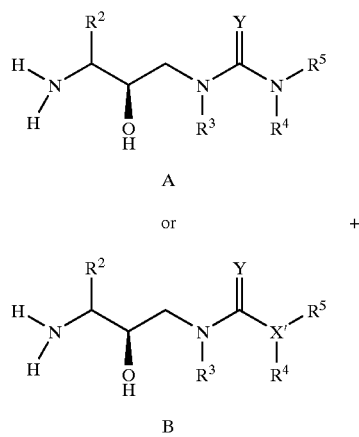

A or +

B

-continued

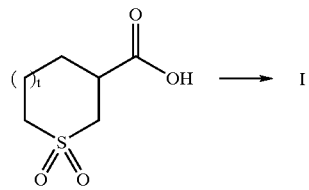

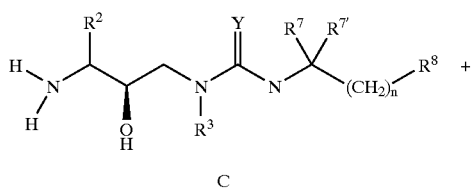

C

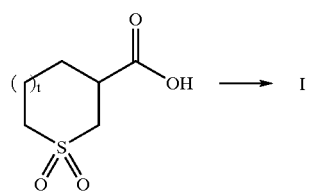

Suitable coupling agents are well-known in the art and include dicyclohexylcarbodiimide or diisopropylcarbodiimide. The coupling is conducted at a temperature of from 20° C. to about 50° C., preferably at about 25° C., in a suitable solvent system such as, for example, N,N-dimethylformamide, and the like. The amino protecting groups are those known in the art and include carbobenzoxy, butyryl, t-butoxycarbonyl, acetyl, benzoyl and the like, preferable carbobenzoxy and t-butoxycarbonyl.

Preparation of the Compounds of Formula II

The cyclic sulfone carboxylic acid is again prepared as set out above in Scheme 1.

An amino epoxide, which is a mixture of diastereomers of the corresponding amino-protected epoxides of the formulas:

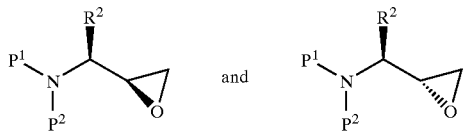 and is prepared by the processes shown in Patent Application Serial Number PCT/US91/8617 and is incorporated by reference therefor. $P^1$ and $P^2$ independently represent hydrogen and amino-protection groups well known in the art and include carbobenzoxy, butyryl, t-butoxycarbonyl, acetyl, benzoyl and the like, preferably carbobenzoxy and t-butoxycarbonyl, acetyl, benzoyl and the like, preferably carbobenzoxy and t-butoxycarbonyl; and $R^2$ represents a radical as set out above. These diastereomers can be separated by chromatography or, alternatively, once reacted in subsequent steps the diastereomeric products can be separated.

The amino epoxide is then reacted, in a suitable solvent system, with an equal amount, of the formula:

$HNR^{4'}R^{5'}$ wherein $R^{4'}$ and $R^{5'}$ are as defined above. The reaction can be conducted over a wide range of temperatures, e.g., from about 60 C to about 120 C in an inert organic solvent, but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dionane and the like, toluene, N,N-dimethylformamide, dimethyl sulfoxide, and mixtures thereof. A preferred solvent is isopropanol. Examples of amines corresponding to the formula $HNR^{4'}R^{5'}$ include those having the following formula:

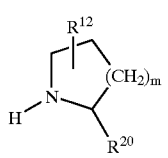 (A)

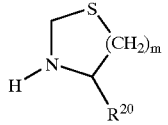 (B)

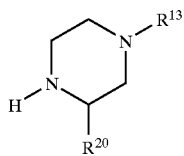 (C)

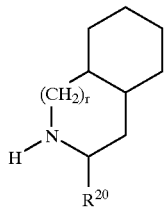 (D)

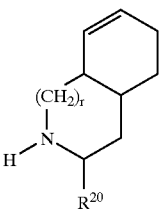 (E)

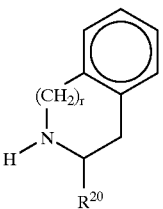 (F)

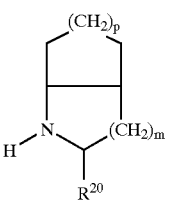 (G)

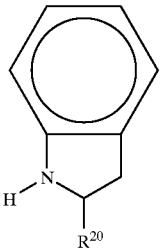 (H)

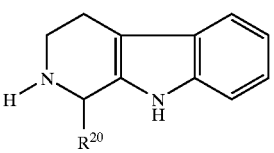 (J)

wherein $R^{20}$, $R^{10}$, $R^{11}$, $R^{12}$, $R^{13}$, m, p and r have the significance given above, and the like. The resulting product is a 3-(N-protected amino)-3-($R^2$)-1-$NR^4R^5$-propan-2-ol derivative (hereinafter referred to as an amino alcohol) is an intermediate which contains the desired N-heterocyclic moiety or intermediate thereof and can be represented by the formula:

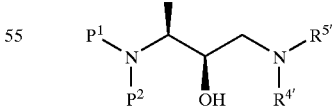

wherein $P^1$, $P^2$, $R^2$, $R^{4'}$ and $R^{5'}$ are as described above.

Alternatively, the compounds of the present invention represented by Formula II above can be prepared utilizing the following general procedure. An N-protected haloketone derivative of an amino acid; also prepared by methods in Patent Application Serial Number PCT/US91/8617 and incorporated by reference therefor, having the formula:

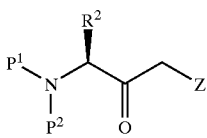

wherein $P^1$ and $P^2$ represent amino protecting groups, $R^2$ is as defined above, and Z represents a chlorine, bromine or iodine atom, is reacted, in a suitable inert organic solvent system, with an equal amount of a desired amine of the formula:

$$HNR^{4'}R^{5'}$$

wherein $R^{4'}$ and $R^{5'}$ are as defined above. The reaction yields a compound of the general formula (5):

Formula 5

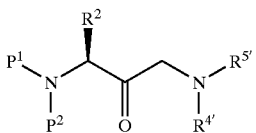

wherein $P^1$, $P^2$, $R^2$, $R^{4'}$ and $R^{5'}$ have the significance given earlier.

The reaction of the N-protected haloketone derivative of an amino acid, preferably one in which $P^1$ and $P^2$ represent benzyloxy carbonyl, with the desired amine, a heterocyclic compound of formula $HNR^4R^5$, can be carried out in any known manner, for example, in an inert organic solvent such as halogenated aliphatic hydrocarbon (e.g., dichloromethane, N,N-dimethylformamide, tetrahydrofuran, isopropanol and ethanol) and in the presence of a base (e.g., a trialkylamine such as triethylamine and diisopropylethyl amine, sodium bicarbonate, DBU and the like, conveniently at about room temperature.

The reduction of the aminoketone compound of Formula 5 results in a compound of the general formula (6):

Formula 6

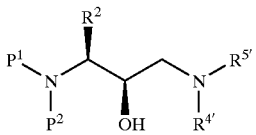

wherein $P^1$, $P^2$, $R^2$, $R^4$ and $R'^{5'}$ have the significance given earlier. The reduction of the aminoketone compound of Formula 5 to the N-heterocyclic moiety-containing derivative (Formula VI) can be carried out according to known methods for the reduction of a carbonyl group to a hydroxy group. Thus, for example, the reduction can be carried out using a complex metal hydride such as an alkali metal borohydride, especially sodium borohydride, in an-appropriate organic solvent such as alkanol (e.g., methanol, ethanol, propanol, isopropanol, etc.).

Conveniently, the reduction is carried out at about room temperature.

Then this N-heterocyclic moiety-containing derivative having an amino protecting group P is or $P^1$ and $P^2$ are, removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is N,N-dibenzyl, these groups may be removed by hydrogenolysis utilizing palladium on carbon.

Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative.

Following neutralization of the salt, the amine is then reacted with a cyclic sulfone carboxylic acid as prepared above to produce the antiviral compounds of the present invention having the formula II also as defined above. The reaction of the amine with a cyclic sulfone carboxylic acid is as shown in the following Scheme 3:

Scheme 3

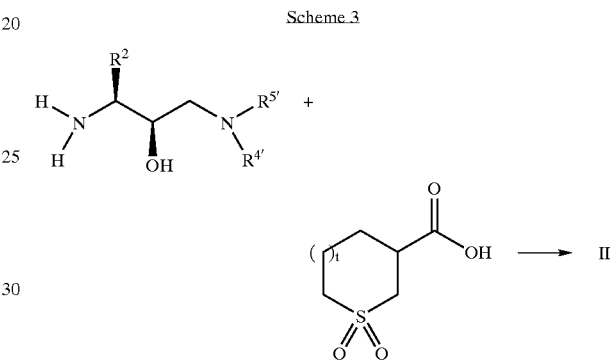

Conditions of the Scheme 3 are generally as follows. The cyclic sulfone carboxylic acid can be coupled to any of the desired isosteres using methods well known to those in the art. For example, activation of the acid can be accomplished using dicyclocarbodiimide or 1-(3-dimethylaminopropyl)-3-ethylcarbodiimide hydrochloride (EDC) in the presence of N-hydroxybenzotriazole in a suitable solvent, such as N,N-dimethylformamide, tetrahydrofuran or methylene chloride. Alternately, the acid can be activated by treatment with N,N-disuccinimidyl carbonate and pyridine. The resulting active esters can then be reacted with the desired isostere, optionally with a base (such as diisopropylethylamine) present, to afford the desired cyclic sulfone containing retroviral protease inhibitors.

The $R^6$ substituent is then added according to the analogous procedures also described in PCT/US91/8613 and WO9208700, incorporated by reference therefor.

Finally, an amino alcohol is prepared by reacting the amino epoxide described above or a corresponding haloalcohol with $R^3NH_2$ also in a manner described in U.S. patent application Ser. No. PCT/US91/8617 incorporated by reference therefor to obtain the compound of the formula:

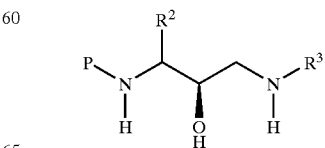

wherein P, $R^2$ and $R^3$ are as defined above.

The amino alcohol defined above is then reacted in a suitable solvent with a sulfonyl chloride ($R^{4}SO_{2}Cl$) or sulfonyl anhydride in the presence of an acid scavenger. Suitable solvents in which the reaction can be conducted include methylene chloride, tetrahydrofuran and the like. Suitable acid scavengers include triethylamine, pyridine and the like. Preferred sulfonyl chlorides are methanesulfonyl chloride and benzenesulfonyl chloride. The resulting sulfonamide derivative can be represented, depending on the epoxide utilized by the formulas:

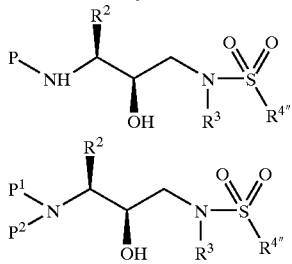

wherein P, $P^1$, $P^2$, $R^2$, $R^3$ and $R^{4''}$ are as defined above.

The sulfonyl halides of the formula $R^{4''}SO_{2}X$ can be prepared by the reaction of a suitable Grignard or alkyl lithium reagent with sulfuryl chloride, or sulfur dioxide followed by oxidation with a halogen, preferably chlorine. Also, thiols may be oxidized to sulfonyl chlorides using chlorine in the presence of water under carefully controlled conditions. Additionally, sulfonic acids may be converted to sulfonyl halides using reagents such as $PCl_5$, and also to anhydrides using suitable dehydrating reagents. The sulfonic acids may in turn be prepared using procedures well known in the art. Such sulfonic acids are also commercially available. In place of the sulfonyl halides, sulfinyl halides ($R^4SOX$) or sulfenyl halides ($R^4SX$) can be utilized to prepare compounds wherein the —$SO_2$— moiety is replaced by an —SO— or —S— moiety, respectively.

A cyclic sulfone of the formula I' wherein Q is represented by (4) or (5) above is prepared in a like manner.

For example, an intermediate, the amino alcohol, is reacted as shown in the following Scheme 3A.

Scheme 3A

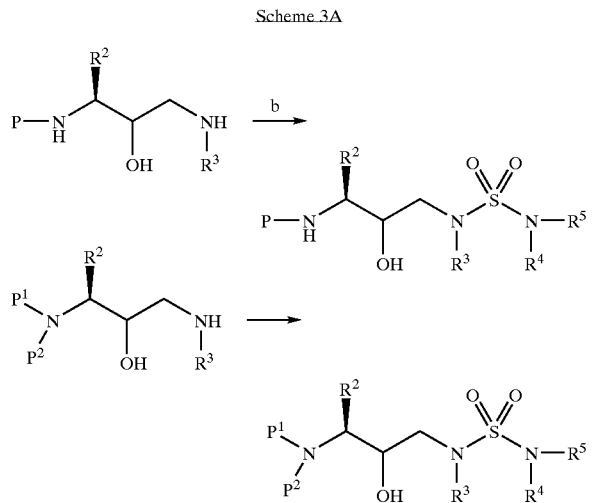

b) sulfamoyl chloride $R^4R^5NSO_2Cl$ (anhydride) + acid scavenger

In other words, the amino alcohol defined above is then reacted in a suitable solvent with a sulfamoyl halide, e.g., sulfamoyl chloride ($R^4R^5NSO_2Cl$ or $R^4HNSO_2Cl$) or corresponding sulfamoyl anhydride in the presence of an acid scavenger. Suitable solvents in which the reaction can be conducted include methylene chloride, tetrahydrofuran. Suitable acid scavengers include triethylamine, pyridine. The resulting sulfamic acid derivative can be represented, depending on the epoxide utilized, by the formulas:

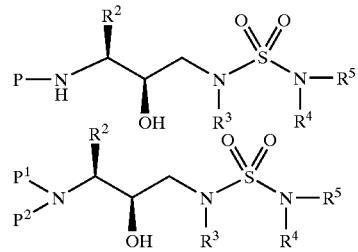

wherein P, $P^1$, $P^2$, $R^2$, $R^3$, $R^4$ and $R^5$ are as defined above. These intermediates are useful for preparing inhibitor compounds of the present invention and are also active inhibitors of retroviral proteases.

The sulfamoyl halides of the formula $R^4NHSO_2X$ can be prepared by the reaction of a suitable isocyanate of the formula $R^4NCO$ with fuming sulfuric acid to produce the corresponding sulfamate which is then converted to the halide by well known procedures, such as by treating the sulfamate with $PCl_5$. Alternatively, the isocyanate can be treated with chlorosulfonic acid to produce the corresponding sulfamoyl chloride directly.

The sulfamoyl halides of the formula $R^4R^5NSO_2Cl$ can be prepared by reacting an amine of the formula $R^4R^5NH$, preferably as a salt such as the hydrochloride, with sulfuryl chloride in a suitable solvent such as acetonitrile. The reaction mixture is gradually warmed to reflux temperature and maintained at the reflux temperature until the reaction is complete. Alternatively, sulfamoyl halides of the formula $R^4R^5NSO_2Cl$ can be prepared by reacting an amine of the formula $R^4R^5NH$ with sulfuryl chloride in boiling MeCN as disclosed in Matier et al., *J. Med. Chem.*, 15, No. 5, p. 538 (1972).

In an analogous manner a sulfamoyl halide, preferably Cl, of the formula:

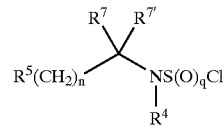

is reacted with the amino alcohol as defined above.

Following preparation of the sulfonamide derivative, the amino protecting group P or $p^1$ and $p^2$ is removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Where the protecting group is a benzyl radical, it an b removed by hydrogenolysis. Following neutralization of the salt, the amine, D, E or F, is then reacted with a cyclic sulfone as described below and shown as follows:

Scheme 4

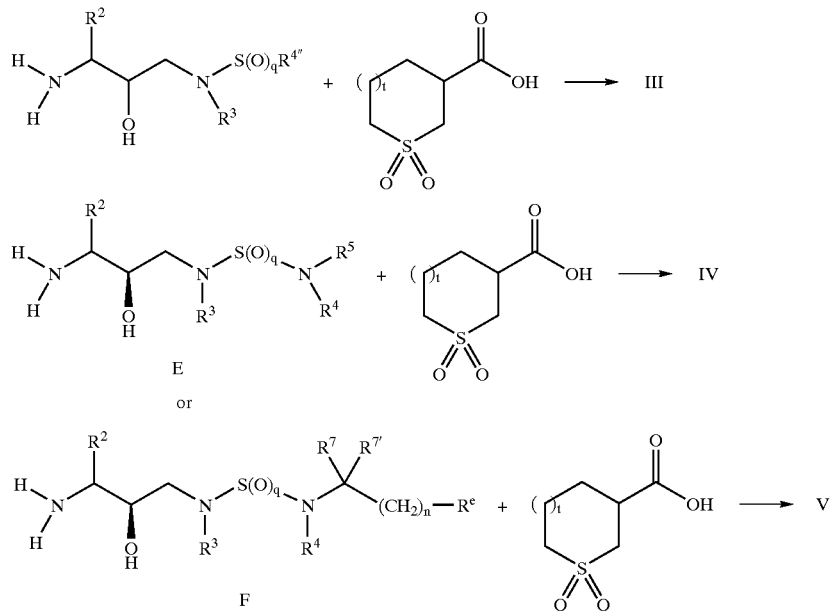

wherein $R^2$, $R^3$, $R^{4''}$ and q is as defined above.

The conditions of the reaction in Scheme 4 include suitable solvent systems, such as, generally, recited following Scheme 3 above.

In order to prepare the tetrahydrothiopyran-4-carboxamide sulfone and its analogs, one can start from the commercially available tetrahydrothiopyran-4-one (compound 1 in Scheme 5). The ketone 1 can be reduced to the alcohol 2 using a variety of methods including sodium borohydride or lithium aluminum hydride. The alcohol can then be converted into a leaving group X, such as chloro, bromo, iodo, O-methanesulfonate, or O-p-toluenesulfonate, of the like. The leaving group X is then displaced with a cyanide source, such as sodium cyanide, potassium cyanide, lithium cyanide or tetra-n-butylammonium cyanide, in a suitable solvent, such as dimethyl sulfoxide, N,N-dimethylformamide or N-methylpyrrolidinone, to provide the cyanide 4. The cyano group can then be hydrolyzed under a variety of conditions well known to those skilled in the art. The hydrolysis to the acid 6 can either be accomplished directly in one step or using a two step procedure involving the amide 5. Thus the cyano compound 4 can be converted to the amide 5 using concentrated sulfuric acid, and the amide converted to the acid using sodium hydroxide or potassium hydroxide in aqueous methanol or ethanol. Alternatively, the cyano compound 4 can be directly hydrolyzed to the acid 6-using concentrated hydrochloric acid at reflux. The sulfur in acid 6 can then be oxidized to the sulfone by various methods, such as, meta-chloroperbenzoic acid, sodium perborate in acetic acid, or hydrogen peroxide in acetic acid, using greater than two equivalents of oxidizing agent. If one desires the sulfoxide, rather than the sulfone, one can use one equivalent of oxidizing agent. The acids 6 and 7 can readily be converted to the compounds of this invention by reaction with various isosteres using standard coupling techniques. It is envisioned that through appropriate modifications of the sequence of reactions in Scheme 5, a variety of analogs can be made with substituents on the tetrahydrothiopyran ring.

Scheme 5

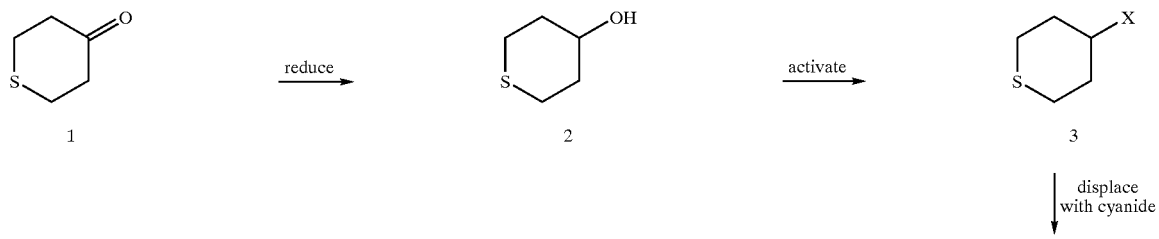

displace with cyanide

-continued

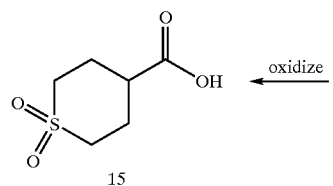 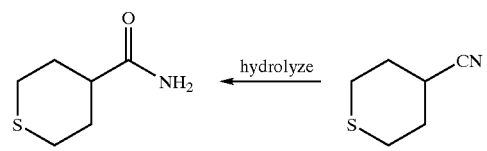

Further, a compound of the present invention wherein W is a heterocyclic ring having a substituent other than hydrogen represented as $R^{40}$, $R^{41}$, $R^{42}$, $R^{43}$, $R^{44}$, $R^{45}$, $R^{46}$, $R^{47}$ or $R^{48}$ can be prepared by the method and Scheme showing the method in the following manner.

In order to prepare the thiomorpholine analog of the cyclic sulfone, as shown in Scheme 6, one can start with either D-, L-, or D,L-cysteine. Reaction of cysteine or an ester of cysteine (compound 8, Scheme 6), where $R_1$ is hydrogen, methyl, ethyl, t-butyl, benzyl or other carboxyl protecting groups with a species $X-CKH_2CO_2R_2$, where X is a leaving group as defined above and $R^2$ is independently hydrogen, methyl, ethyl, t-butyl, benzyl or other carboxyl protecting groups, in the presence of a base such as sodium bicarbonate, triethylamine, or the like provides the cyclic sulfide 9. The sulfide 9 can then be oxidized to either the sulfoxide or sulfone using the methods described above. If necessary, the carboxyl protecting group can be removed from 9 or 10 and the resulting carboxylic acid coupled to the various isosteres using standard methods. It is also envisioned that one could use D-, L- or D<L-penicillamine [$HSC(CH_3)_2CH(NH^2)CO^2H$] in place of cysteine 8. It is also contemplated that appropriate modifications of the sequence would provide a variety of analogs.

Scheme 6

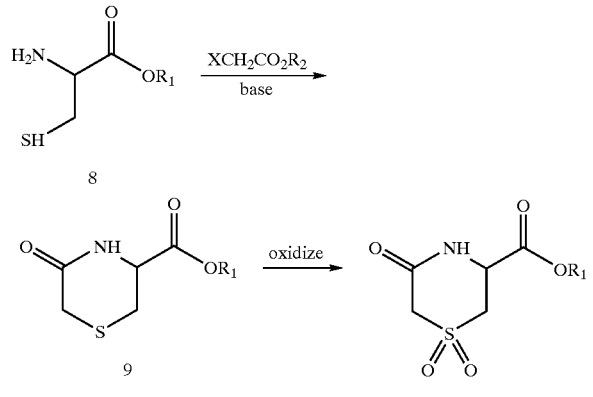

For compounds wherein the oxidation state of the cyclic sulfur in the W substituent is within that of the desired product, the oxidation of Schemes 1 and 1a can be performed with a suitable oxidizing agent; such as hydrogen peroxide, sodium perborate or meta-chloroperbenzoic acid. It is well known to those skilled in the art that this oxidation can be cotrolled through the use of one equivalent of oxidizing agent to provide the sulfoxide or at least two or more equivalents to provide the the sulfone.

Where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable form known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, melting points were determined on a Fisher-Johns melting point apparatus and are uncorrected. All reagents were used as received without purification. All proton and carbon NMR spectra were obtained on either a Varian VXR-300 or VXR-400 nuclear magnetic resonance spectrometer using tetramethylsilane as internal standard. Gas chromatograph was performed on a Varian 3400 chromatography system. All instruments were utilized according to the manufacturer's directions.

EXAMPLES

Example 1

Preparation of the Cyclic Sulfone Carboxylic Acid of the Formula:

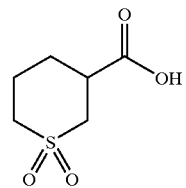

Part A: Preparation of methyl tetrahydro-2H-thiopyran-4-keto-3-carboxylate.

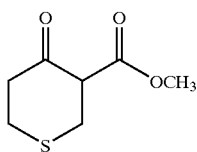

To a suspension of 55.1 gm (1.02 mole) of dry, powdered sodium methoxide in anhydrous ether (200 mL) at 0° C. was added 56.8 mL (0.33 mole) dimethyl 3,3-thiodipropionate dropwise. The reaction mixture was stirred under nitrogen, warming to room temperature over 1 hour, and then refluxed for 4.5 hrs. Subsequently, the suspension was stirred at room temperature for 17 hrs. upon which was added a solution of acetic acid (100 mL) in $H_2O$ (300 mL) slowly at 0° C. The aqueous layer was extracted three times with diethylether. The combined ether layers were washed three times with saturated sodium bicarbonate and one time with saturated sodium chloride. The organic layer was dried with $MgSO_4$ and concentrated in vacuo to give a pale yellow oil which was partially purified by vacuum distillation to give 21.11 gm (114–124° fraction/1.5 mm) of oil which was further purified by flash chromatography on 1 kg silica gel with 4–5% ethyl acetate in hexane to give 19.48 gm (34%) pure oil which crystallized upon standing; mass spectrum m/e= 174 (EI,M+).

Part B: Preparation of methyl tetrahydro-2H-thiopyran-4-hydroxy-3-carboxylate.

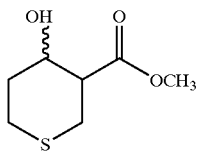

To a −78° C. solution of 5.91 gm (0.0339 moles) of methyl tetrahydro-2H-thiopyran-4-keto-3-carboxylate in anhydrous methylene chloride (100 mL) and anhydrous methanol (100 mL) was added 0.644 gm (0.017 mole) soldium borohydride under $N_2$ over a period of 6 hrs. The reactor was alloed to warm to 0° C. over 1 hr upon which was added $H_2O$ (100 mL), slowly at first. The organnic solvents were removed in vacuo. The aqueous residue was extracted 4 times with methylene chloride. The combined organic extracts were dried over magnesium sulfate, filtered, and concentrated in vacuo to give 4.93 gm (83% crude yield) of a 2:1 mixture of cis; trans methyl tetrahydro-2H-thriopyran-4-hydroxy-3-carboxylate as an oil; mass spectrum m/e=176(EI,M+).

Part C: Preparation of methyl 5,6-dihydro-2H-thiopyran-3-carboxylate.

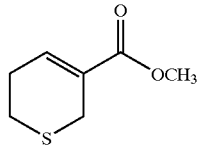

To a solution of 4.93 gm (0.0279 mole) of methyl tetrahydro-2H-thiopyran-4-hydroxy-3-carboxylate from part B in anhydrous methylene chloride (25 mL) was added 6.77 mL (0.0837 mole) anhydrous pyridine. The solution was cooled to 0° C., upon which was added 3.25 mL (0.0420 mole) methanesulfonyl chloride, dropwise via syringe. The solution was allowed to warm to room temperature and stirred under $N_2$ for 7.5 hrs. The reaction was then cooled to 0° C. and an additional 0.648 mL (0.00837 mole) of methanesulfonyl chloride was added. The solution was stirred at room temperature an additional 16 hrs. upon which ethyl acetate (125 mL) was added. The organic layer was washed with dilute HCl, saturated sodium bicarbonate, and saturated sodium chloride, dried over magnesium sulfate, filtered, and concentrated in vacuo to give a mixture of the cis and trans mesylate and unreacted methanesulfonyl chloride. The crude mesylate mixture was dissolved in anhydrous methylene chloride (30 mL) upon which was added 12.68 mL (0.0911 mole) triethyl amine. The reaction was stirred under $N_2$ for 7 hrs. upon which was added 8.5 mL (0.061 mole) triethyl amine and the solution stirred 17 more hrs. The organic layer was washed once with dilute acid and once with saturated sodium chloride, dried over magnesium sulfate, filtered, and concentrated in vacuo. The crude material was purified by flash chromatography on 300 gm silica gel with 4–25% ethyl acetate in hexane to give 2.76 gm (63%) of methyl 5,6-dihydro-2H-thiopyran-3-carboxylate as a clear oil; mass spectrum m/z=159 (CI,M+H)

Part D: Preparation of Methyl 5,6-dihydro-2H-thiopyran-3-carboxylate, 1,1 Dioxide.

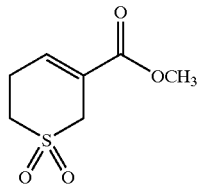

To a solution of 0.934 gm (5.75 mmol) of 5,6-dihydro-2H-thiopyran-3-carboxylate from part C in glacial acetic acid (40 mL) was added 1.98 gm (12.88 mmole) sodium perborate. The reaction mixture was stirred at 55° C. under $N_2$ for 19 hrs. whereupon the solution was poured into $H_2O$ (50 mL) and neutralized with 50% NaOH to pH=7. The solution was extracted three times with methylene chloride. The combined organic layers were washed once with saturated sodium bicarbonate and once with saturated sodium chloride, dried over magnesium sulfate, filtered and concentrated in vacuo to give 0.832 gm (76%) of methyl 5,6-dihydro-2H-thiopyran-3-carboxylate, 1,1 dioxide as a white solid; mass spectrum m/e=190 (EI, M+)

Part E: Preparation of Methyl-2H-thiopyran-3-carboxylate, 1,1-dioxide.

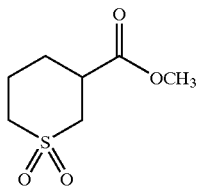

A solution of 832 mg (4.37 mmole) of 5,6-dihydro-2H-thiopyran-3-carboxylate, 1,1 dioxide from part D in methanol (40 mL) was hydrogenated in the presence of 400 mg (50% wt) of 10% Pd/charcoal for 4 hrs. at room temperature and 50 psig of $H_2$. The catalyst was removed by vacuum filtration through a short plug of packed celite and the solvent removed in vacuo to give 802 mg (96%) of methyl 2H-thiopyran-3-carboxylate, 1,1-dioxide as a white solid; mass spectrum m/z=193 (CI,M+H)

Part F: Preparation of 2H-thiopyran-3-carboxylate, 1,1-dioxide.

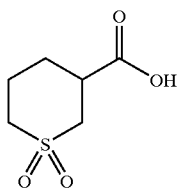

To a solution of 789 mg (4.10 mmole) of methyl 2H-thiopyran-3-carboxylate, 1,1-dioxide from part E in 4N HCl/dioxane (10 mL) was added $H_2O$ (5 mL) slowly. The reaction was stirred at room temperature for 116 hrs. whereupon the solvent was removed in vacuo. The crude material was recrystallized from a mixture of ethyl acetate and hexane to give 613 mg (84%) of 2H-thiopyran-3-carboxylate,1,1-dioxide as a white solid; mass spectrum m/z=179 (CI, EI, M+H)

Alternatively, one can separate the isomers from part B.

Part B2: Preparation of cis methyl tetrahydro-2H-thiopyran-4-hydroxy-3-carboxylate.

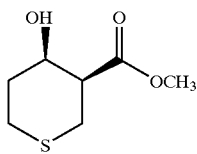

To a −78° C. solution of 6.01 gm (0.0345 mol) of methyl tetrahydro-2H-thiopyran-4-keto-3-carboxylate from part A in anhydrous methylene chloride (100 mL) and anhydrous methanol (100 mL) was added 0.65 gm (0.0172 mol) sodium borohydride under $N_2$ over a period of 3 hrs. The reaction was allowed to warm to 0° C. over 1 hour upon which was added $H_2O$ (100 mL), slowly at first. The organic solvents were removed in vacuo. The aqueous residue was extracted 4 times with methylene chloride. The combined organic extracts were dried over magnesium sulfate, filtered, and concentrated in vacuo. The crude material was purified by flash chromatography on 300 gm silica gel and diluted with 1 to 1.5% methanol in methylene chloride to give 1.80 gm (30%) of the cis isomer as a clear oil; mass spectrum m/z=177 (FAB,M+H)

Part C2: Preparation of methyl 5,6-dihydro-2H-thiopyran-3-carboxylate.

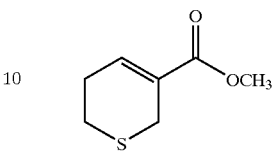

To a solution of 1.79 gm (0.0101 mol) of cis-methyl tetrahydro-2H-thiopyran-4-hydroxy-3-carboxylate from part B2 in anhydrous methylene chloride (10 mL) was added 2.45 mL (0.0303 mol) anhydrous pyridine. The solution was cooled to 0° C., upon which was added 1.18 mL (0.0152 mol) methanesulfonyl chloride, dropwise via syringe. The solution was allowed to warm to room temperature and stirred under $N_2$ for 4 hrs., whereupon the reaction was cooled to 0° C. and an additional 1.6 mL (0.020 mol) anhydrous pyridine and 1.18 mL (0.0152 mol) methanesulfonyl chloride were added. The solution was stirred at room temperature for 48 hrs. upon which ethyl acetate (50 mL) was added. The organic layer was washed with dilute HCl, saturated sodium bicarbonate, and saturated sodium chloride, dried over magnesium sulfate, filtered and concentrated in vacuo. The crude material was purified by flash chromatography on 200 gm silica with 20–33% ethyl acetate in hexane to give 2.18 gm (85%) of the cis mesylate which crystallized upon standing. The pure mesylate (2.15 gm; 8.45 mmol) was dissolved in anhydrous methylene chloride (8 mL) upon which was added 3.53 mL (25.3 mmol) of triethyl amine and the solution stirred for 17 hrs. An additional 2.35 mL (16.9 mmol) of triethyl amine was added and the reaction stirred for 2 more hrs. The organic layer was washed with dilute HCl and saturated sodium chloride, dried over magnesium sulfate, filtered, and concentrated in vacuo to give 1.29 gm (96%) of methyl 5,6-2H-thiopyran-3-carboxylate as a clear oil; mass spectrum m/z=159 (CI,M+H), which was identical to the material from part C of example 1.

Example 2

Preparation of tetrahydrothiophene-3-carboxylic acid, 1,1-dioxide.

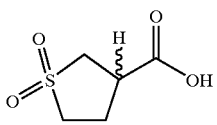

Part A: Preparation of methyl tetrahydrothiophene-3-carboxylic Acid, 1,1-dioxide.

To 3-methoxycarbonyl-2,5-dihydrothiophene-1,1-dioxide (5.0 g, $2.9 \times 10^{-2}$ mol) in deoxygenated MeOH (60 ml) was added 10% Pd on carbon (0.5 g) and the resulting suspension hydrogenated at 50 psi for 48 hours. Subsequently, the catalyst was removed by filtration through celite, and the filtrate concentrated in vacuo to give a pale oil (4.23 g, 84%); mass spectrum, m/z 179 (CI, M+H).

Part B: Preparation of tetrahydrothiophene-3-carboxylic Acid, 1,1-dioxide.

To the ester from part A (4.23 g, 2.4×10⁻² mol) in MeOH (75 ml) at 0° C. was added lithium hydroxide (1.01 g, 2.4×10⁻² mol) in water (80 ml) and the resulting solution stirred, warming to ambient temperature over 6.5 hours. The MeOH was removed in vacuo and the residue neutralized with 2.5N NaOH and extracted repeatedly with CH₂Cl₂. The combined organic extracts were dried over MgSO₄, filtered, and concentrated in vacuo to give an oil which was triturated in CH₃OH (25 ml). The solids were removed by filtration and the filtrate concentrated in vacuo to give a pale oil (0.57 g, 15%); mass spectrum, n/z 165 (CI, M+H).

Example 3

[1S-[1R*(R*),2S*]]-N¹[3-[[[(1,1-dimethylethyl)amino] carbonyl](3-methylbutyl)amino]-1-hydroxy-1-(phenyl-methyl)propyl]-2-amino]butanediamide

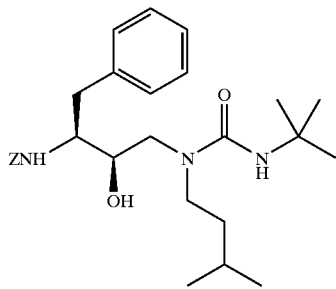

Protected [1S-[1R*(R*), 2S*]]-N¹[3-[[[(1,1-dimethylethyl) amino]carbonyl](3-methylbutyl)amino]-1-hydroxy-1-(phenyl-methyl)propyl]-2-amino)butanediamide is prepared by methods disclosed or methods analogous therein PCT/US91/8613 which is incorporated by reference therefor.

Example 4

Preparation of 2H-thiopyran-3-carboxamide, N-[3-[[[(1, 1-dimethylethyl amino]-carbonyl](3-methylbutyl)amino]-2-hydroxy-1-(phenylmethyl)propyl)tetrahydro,-1,1-dioxide.

3S-[3R*(1R*,2S*)]]-

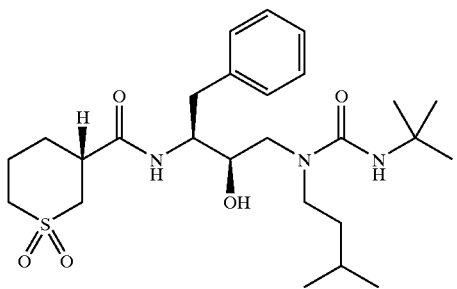

and

[3R-[3R*(1R*,2S*)]]-

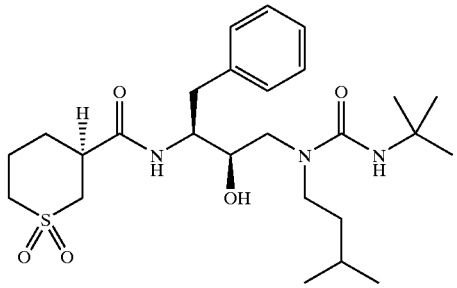

Part A

The following amine is prepared by deprotecting the compound prepared in Example 3 above by procedures disclosed in PCT/US91/8613.

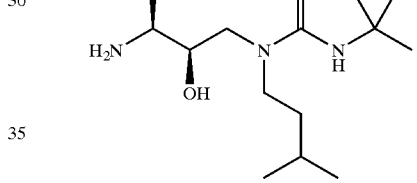

Part B:

To a 0° C. solution of 93.5 mg (0.525 mmole) of 2H-thiopyran-3-carboxylate, 1,1-dioxide in anhydrous dimethyl formamide (1 mL) was added 115 mg (0.75 mmole) of hydroxybenzotriazole and 105 mg (0.55 mmole) of 1-(3-dimethylaminopropyl)-3-ethylcarbodiimide hydrochloride (EDC). The solution was stirred under N₂ for 2 hrs. at 0° C. upon which was added 175 mg (0.50 mmole) of amine from part A and stirring continued for 48 hrs. at room temperature. The solvent was removed in vacuo and redissolved in ethyl acetate whereupon it was washed with 5% citric acid, saturated sodium bicarbonate, and saturated sodium chloride. The organic layer was dried with magnesium sulfate, filtered and concentrated in vacuo to give 214 mg (84% of crude material.

The 2 diastereomers were purified by flash chromatography on 21 grams of silica gel and eluted with 50–85% ethyl acetate in hexane to give 30 mg of each diasteromer as a white solid; mass spectrum upper spot m/z=516 (FAB,M+Li)

lower spot m/z=516 (FAB,M+Li)

Example 4a

In an analogous manner using appropriate corresponding starting materials a compound of the following formula is prepared.

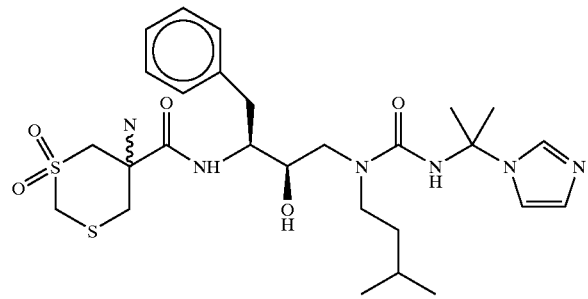

Example 5

Preparation of thiophene-3-carboxamide, N-[3-[[[(1,1-dimethylethyl)amino]-carbonyl](3-methylbutyl)amino]-2-hydroxy-1-(phenylmethyl)propyl]tetrahydro,-1,1-dioxide, [3S-[3R*(1R*,2S*]]- and

Preparation of thiophene-3-carboxamide, N-(3-[[[(1,1-dimethylethyl)amino]-carbonyl](3-methylbutyl)amino]-2-hydroxy-1-(phenylmethyl)propyl)tetrahydro,-1,1-dioxide, [3R-[3R*(1R*,2S*)]]-

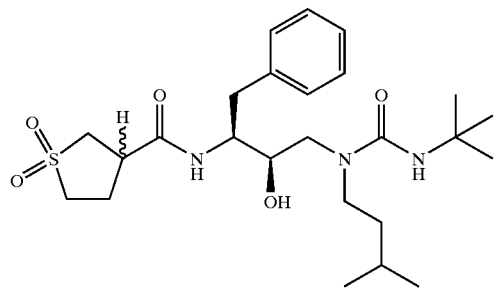

(and its isomer)

To the acid from Preparation 2 (0.25 g, 1.5×10⁻³ mol) in anhydrous DMF (3 ml) was added hydroxy-benzotriazole (0.40 g, 3.0×10⁻³ mol) and 1-(3-dimethylaminopropyl)-3-ethylcarbodi-imide hydrochloride (0.41 g, 2.1×10⁻³ mol) and the resulting solution stirred for 5 minutes. Subsequently was added the amine from Example 4 Part A (0.44 g, 1.3×10⁻³ mol) in anhydrous DMF (4 ml) and the reaction mixture stirred under a nitrogen atmosphere for 23 hours, upon which it was poured into 60% saturated NaHCO₃ solution (120 ml), chilled for 3 hours, and the resulting precipitate isolated via vacuum filtration. The tacky precipitate was taken into CH₂Cl₂, washed with KHSO₄ (aq), dried over MgSO₄, recrystallized from EtOAc/hexanes to give a white solid (0.26 g, 42%); mass spectrum, m/z 502 (FAB, M+Li).

Example 6

Preparation of [3-[3-[[(1,1-dimethylethyl)amino]carbonyl]octahydro-2(1H)-isoquinolinyl]-2-hydroxy-1-(phenylmethyl)propyl, phenylmethyl ester, [3S-[2(1R*,2S*),3α4αβ, 8αβ]]-

Preparation of N-Benzyloxycarbonyl-3(S)-amino-1,2(S)-epoxy-4-phenylbutane.

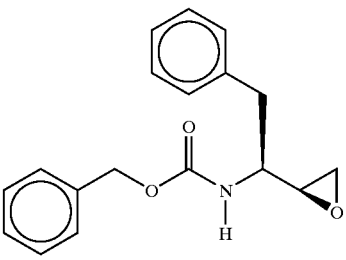

Part A

To a solution of 75.0 g (0.226 mol of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed in vacuo at 40° C. and the residue dissolved in ethyl acetate (approx. 1L). The solution was washed sequentially with 1M potassium hydrogen sulfate, saturated sodium bicarbonate and then saturated sodium chloride solutions. After drying over anhydrous magnesium sulfate and filtering, the solution was removed in vacuo. To the resulting oil was added hexane (approx. 1L) and the mixture warmed to 60° C. with swirling. After cooling to room temperature, the solids were collected and washed with 2L of hexane. The resulting solid was recrystallized from hot ethyl acetate and hexane to afford 32.3 g (43% yield) of N-benzyloxycarbonyl-3(S)-amino-1-chloro-4-phenyl-2(S-butanol, mp 150–151° C. and M+Li⁺=340. formula:

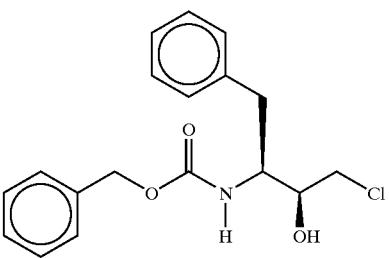

Part B:

To a solution of 6.52 g (0.116 mol, 1.2 equiv.) of potassium hydroxide in 969 mL of absolute ethanol at room temperature, was added 32.3 g (0.097 mol) of N-CBZ-3(S)-amino-1-chloro-4-phenyl-2(S)-butanol, wherein CBZ stands for benzyloxycarbonyl. After stirring for fifteen minutes, the solvent was removed in vacuo and the solids dissolved in methylene chloride. After washing with water, drying over magnesium sulfate (MgSO₄), filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102–103° C. and MH⁺ 298; formula:

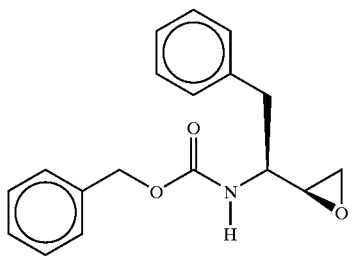

Preparation of carbamic acid, [3-[3-[[(1,1-dimethylethyl)amino]carbonyl]octahydro-2(1H)-isoquinolinyl]-2-hydroxy-1-(phenylmethyl)propyl]-,phenylmethyl ester, [3S-[2(1R*,2S*), 3α, 4αβ, 8αβ]]-, also known as carbamic acid, [3S-[3-[[(1,1-dimethylethyl)amino]carbonyl]decahydroisoquinolinyl]-2-hydroxy-2-(phenylmethyl)propyl]-, phenylmethyl ester, [3S-[2(1R*,2S*), 3α, 4αβ, 8αβ]]-.

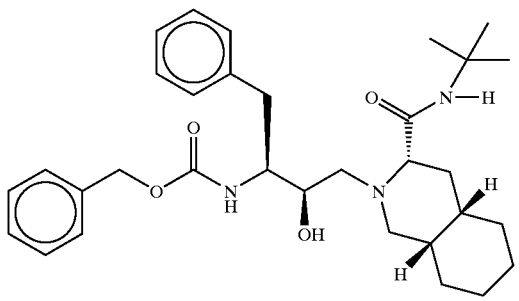

Part A:

L-tetrahydroisoquinoline-2-carboxylic acid (24.83 g, 0.140 mol) was suspended in a solution of 80 mL of 2.5 N sodium hydroxide, 80 mL of water, and 80 mL of tetrahydrofuran. To this was added with vigorous stirring, 32.0 g (0.147 mol) of tert-butylpyrocarbonate in 20 mL of tetrahydrofuran. After 1 hour the pH dropped from 13 to 8.2, at pH=7.8 sodium hydroxide (1.5 N) was added dropwise to maintain a pH of 8.8. After the pH stabilized, the contents were extracted with diethylether (2×125 mL). The aqueous phase was acidified (pH~2.0) with more HCl, after cooling the solution in an ice bath. The precipitate was extracted with ether, which was then dried over MgSO$_4$, filtered and concentrated to yield 36.8 grams of crude product which needed no purification (95% yield). The product was N-tert-butoxycarbonyl-L-tetrahydroisoquinoline -2-carboxylic acid which has the following formula:

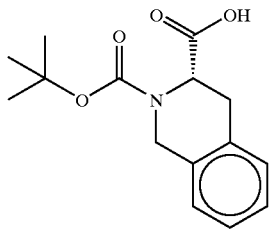

Part B:

N-tert-butoxycarbonyl-L-tetrahydroisoquinoline-2-carboxylic acid (27.7 g, 0.10 moles) was dissolved in 50 mL of dimethylformamide, and to this was added a warmed solution of 21 g of N-hydroxybenzotriazole in 30 mL of dimethylformamide. The solution was cooled to 10° C. and to this was added 19.1 g (0.10 moles) of 1-(3-dimethylaminopropyl)-2-ethylcarbodiimide hydrochloride (EDC) and the solution stirred for 10–15 minutes, at which time 7.3 g (0.100 moles) of distilled tert-butylamine was added. After 14 hours the solution was concentrated and 200 mL of ethyl acetate was added. The organic layer was washed with 5% aqueous potassium hydrogen sulfate, saturated sodium bicarbonate and brine, dried over magnesium sulfate, filtered, and concentrated to yield a yellow oil, which was crystallized from warm hexane to yield 15.0 grams of a first crop 45.5% yield. The product was N-tert-butoxycarbonyl-S-tetrahydroisoquinoline-2-carboxylic acid tertbutyl amide which has the following formula:

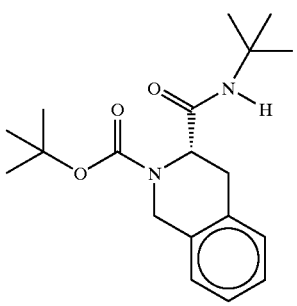

Part C:

N-tert-butoxycarbonyl-S-tetrahydroisoquinoline-2-carboxylic acid tertbutyl amide (10.0 g, 30 mmol) was dissolved in 50 mL of methanol and placed in a Fischer Porter bottle with 3.2 g of wet rhodium (50 wt % H$_2$O, 10 wt % rhodium on carbon). The bottle was purged with nitrogen, and charged with 50 psig hydrogen and heated to 50° C. for 24 hours. The catalyst was removed by filtration and the methanol evaporated to yield a mixture of (S,S,S) desired isomer and (S,R.R) undesired isomer in a 2:1 ratio, respectively. The desired isomer (S,S,S,) was separated by column chromatography on silica gel using a 15–20% ethylacetate hexane gradient elution to yield 6.1 grams of pure isomer (66% yield). The product was N-tert-butyloxycarbonyl-(S,S,S)decahydroisoquinoline-2-carboxylic acid, tert-butylamide which has the following structure:

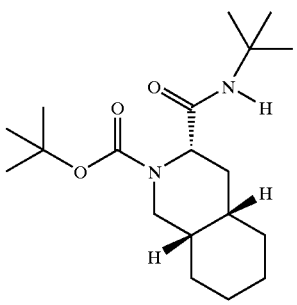

Part D:

N-tert-butyloxycarbonyl-(S,S,S)decahydroisoquinoline-2-carboxylic acid, tert-butylamide (6.3 g, 18.6 mmol) was dissolved in 30 mL of 4N HCl in dioxane and stirred under a nitrogen atmosphere for 1 hour. The solvent was removed and the white solid was suspended in 200 mL of dichloromethane and washed several times with saturated sodium bicarbonate. The dichloromethane (CH₂Cl₂) layer was dried over magnesium sulfate, filtered, and concentrated to yield 3.68 g of freebase (85% yield). The amine product has the following structure:

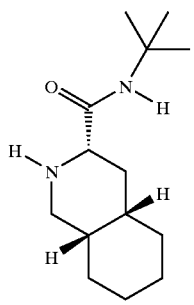

Part E:

The amine from D (3.68 g, 15.4 mmol) and 4.58 g (15.4 mmol) of epoxide from Example 1 were dissolved in 50 mL of isopropanol and refluxed under a nitrogen atmosphere for 48 hours. The isopropanol was removed and the crude solid was chromatographed on silica gel using methanol methylene chloride eluant to provide 8.0 g of pure product (97% yield) identified as carbamic acid, [3-[3-[[(1,1-dimethylethyl)amino]-carbonyl]octahydro-2(1H)-isoquinolinyl]-2-hydroxy-1-(phenylmethyl)-propyl]-, phenylmethyl ester, [3S-[2(1R*,2S*), 3α, 4αβ, 8αβ]].

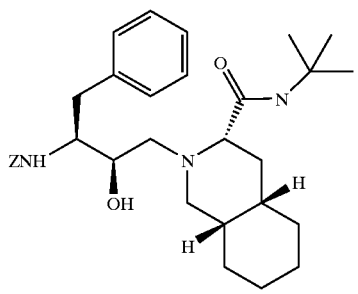

Example 7

Synthesis of

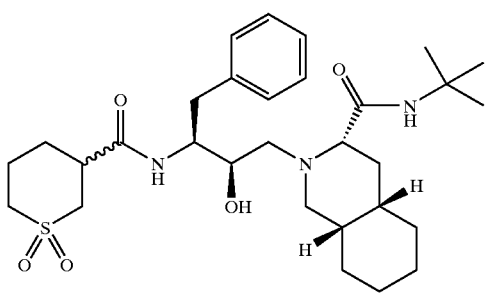

Part A:

A solution of carbamic acid, [3-[3-[[(1,1-dimethylethyl)amino]-carbonyl] octahydro-2(1H)-isoquinolinyl]-2-hydroxy-1-(phenylmethyl)-propyl]-phenylmethylester, [3S-[2(1R*,2S*),3, 4αβ, 8αβ]]- (1.01 gm, 1.89 mmole) in N₂ purged THF (20 mL) was hydrogenated in the presence of 0.50 gm (50% wt) of 10% Pd/charcoal for 17 hrs at 50 psig of H₂. The catalyst was removed by vacuum filtration through a short plug of packed celite and the solvent was removed in vacuo to give 759 mg (100%) of a white foam. The amine product has the following formula:

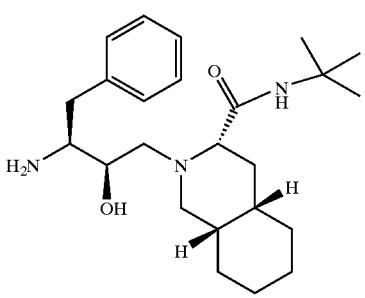

Part B:

To a solution of 100 mg (0.561 mmole) of 2H-thiopyran-3-carboxylate, 1,1-dioxide in anhydrous methylene chloride (2.5 mL) was added 143.7 mg (0.561 mmole) of N,N disuccinimidyl carbonate and 45.4 μl (0.561 mmole) pyridine. Subsequently, 1 mL acetonitrile was added to form a homogeneous solution. The resulting solution was stirred under N₂ for 3 hrs. The solvent was removed in vacuo and redissolved in ethyl acetate, whereupon it was washed with saturated sodium bicarbonate, 5% KHSO₄, and saturated sodium chloride. The organic layer was dried with magnesium sulfate, filtered, and concentrated in vacuo to give 63.2 mg (41%) of as a white solid; mass spectrum m/z 282 (FAB,M+Li) having the following structure:

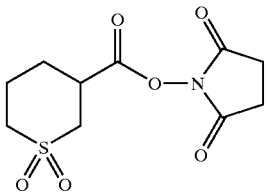

Part C:

To a solution of 57 mg (0.207 mmole) of hydroxysuccinimide ester from Part B in 1.8 mL methylene chloride and 1.2 mL of THF was added 83.15 mg (0.207 mmole) of amine from Part A. the reaction was stirred for 19.5 hrs whereupon the solvent was removed in vacuo. The crude product was chromatographed on 10 gm silica gel with 3% methanol in methylene chloride to give 90.2 mg (78% of as a white powder; mass spectrum m/z 568 (FAB,M+Li)

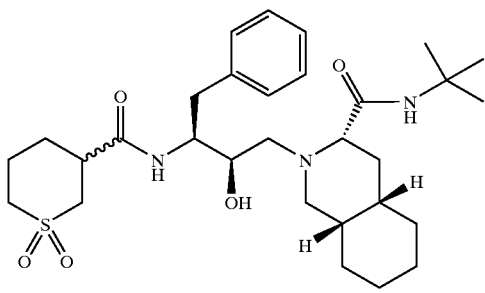

Example 8

Part A:

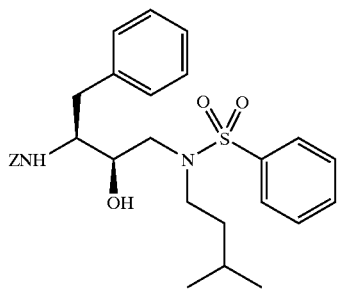

Preparation of phenylmethyl [2R-hydroxy-3-[(3-methylbutyl)(phenylsulfonyl)amino]-1S-(phenylmethyl)propyl]carbamate From the reaction of N[3(S)-benzyloxycarbonylamino-2(R)-hydroxy-4-phenylbutyl) N-isoamylamine (1.47 μm, 3.8 mmol), triethylamine (528 uL, 3.8 mmol) and benzenesulfonyl chloride (483 uL, 3.8 mmol) one obtains phenylmethyl (2R-hydroxy-3-[(3-methylbutyl)(phenylsulfonyl)amino]-1S-(phenylmethyl)propyl]carbamate. Column chromatography onsilica gel eluting with chloroform containing 1% ethanol afforded the pure product. Anal. Calcd. for $C_{29}H_{36}N_2O_5S$: C, 66.39; H, 6.92; N, 5.34. Found: C, 66.37; H, 6.93; N, 5.26.

Part B:

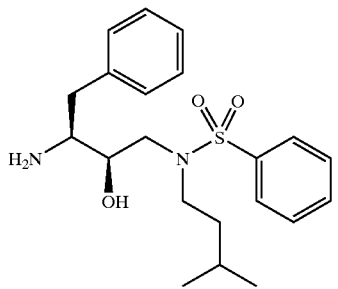

A solution of 10.1 gm (19.2 mmole) of phenylmethyl ester of the carbamic acid from Part A above in $N_2$ purged MeOH (100 ml) was hydrogenated in the presence of 2 gm (20% wt) of 10% Pd/charcoal for 6 hrs. at 50 psig of Hz. The catalyst was removed by vacuum filtration through a short plug of packed celite and the solvent was removed in vacuo to give 7.41 gm (99%) of amine; mass spectrum, m/z=391 (FAB, M+H).

Part C:
Preparation of:

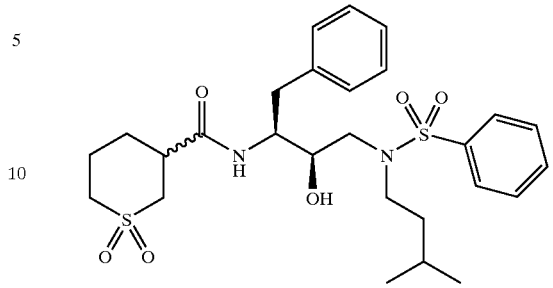

To a solution of 190 mg (1.07 mmole) of 2H-thiopyran-3-carboxylate, 1,1-dioxide in anhydrous DMF (3 mL) was added 240 mg (1.56 mmole) N-hydoxybenzotriazole and 280 mg (1.46 mmole) of 1-(3-dimethyl aminopropyl)-3-ethyl carbodiimide hydrochloride (EDC). The resulting solution was stirred under nitrogen for 10 minutes at room temperature upon which was added 290 mg (0.91 mmole) of amine from Part B in DMF (5 ml) and stirring continued for 18 hrs. Subsequently, the reaction mixture was poured into 50% saturated sodium bicarbonate (aq) and extracted into ethyl acetate. The combined organic layers were dried over magnesium sulfate, filtered and concentrated in vacuo. The crude material was recrystallized from ethylacetate/diethylether/hexane to give 300 mg (60%) of a 1:1 mixture of

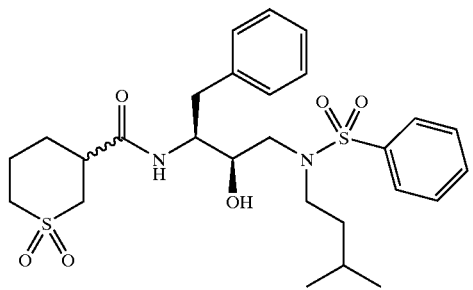

as a white powder; mass spectrum m/z=557 (FAB, M+Li)

Example 9

Preparation of

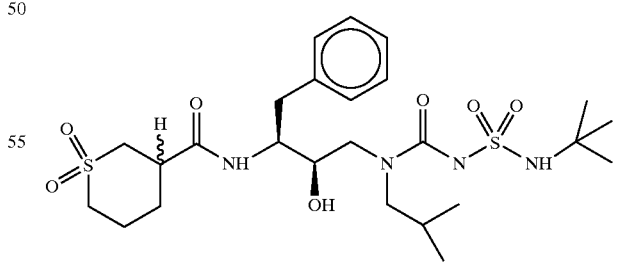

Part A

A 25 mL two-necked RB flask, equipped with a reflux condenser and dropping funnel and under a nitrogen atmosphere, was charged with t-butanol (207 uL, 2.2 mmoles) and 5 mL of hexane. Chlorosulfonyl isocyanate (192 uL, 2.2 mmoles) in 3 mL of hexane was added dropwise. Upon warming a homogeneous solution was obtained. The solution was heated at gentle reflux for 45 min., then was cooled to r.t. Solvent was removed under a steady stream of nitrogen. The crude t-butyl sulfamoyl chloride (a liquid) was used without further purification.

Part B

A solution of N-benzyloxycarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl] N-isobutylamine, mp 108.0–109.5° C., MH+m/z=371.

Part C

N[3 (S)-benzyloxycarbonylamino-2 (R)-hydroxy-4-phenylbutyl]-N-isobutylamine (370 mg, 1.0 mmole) from Part B was mixed with DIEA (139 uL, 1 mmol) in 5 mL of dichloromethane. Chlorotrimethylsilane (126 uL, 1 mmole) was added. After 1 h., additional DIEA (160 uL) was added, followed by a dichloromethane solution (5 mL) containing 1.1 mmole of t-butyl sulfamoyl chloride from Part A. The reaction mixture was stirred for 2 days. Solvent was removed under aspirator pressure. The oily residue was taken p in ethyl acetate and washed with 5% citric acid, saturated sodium bicarbonate, brine, dried over sodium sulfate and evaporated to an oily residue (380 mg).

The crude product was stirred in 4N HCl in dioxane (6 mL) for 15 min. After the addition of 4 mL of methanol to the reaction mixture, the solution was stirred for an additional 15 min., then concentrated to an oily residue. The product, phenylmethyl [2R-hydroxy-3-[[(1,1-dimethylethyl)amino]sulfonyl](2-an oily residue. The product, phenylmethyl [2R-hydroxy-3-[[(1,1-dimethylethyl)amino]sulfonyl](2-methylpropyl)amino]-1S-(phenylmethyl)propyl] carbamate was obtained after silica gel chromatography (188 mg, 37%). MS (MH)+=506. The carbobenzoxy group was then removed via hydrogenolysis in ethanol over 10% palladium on carbon and under 40 psig hydrogen and the resulting amine used directly in the next step.

Part D

To a solution of 42.2 mg (0.24 mmol)(of racemic 2H-thiopyran-3-carboxylic acid, 1,1-dioxide in 1.0 mL of anhydrous N,N-dimethylformamide (DMF) and 52 mg (0.34 mmol) of N-hydroxybenzotriazole, was added 47 mg (0.25 mmol) of 1-(3-dimethylaminopropyl)-3-ethylcarbodiimide hydrochloride at 0° C. After two hours at 0° C., a solution of 84 mg (0.23 mmol) of free amine from Part C in 0.5 mL of DMF was added and the reaction stirred for three days at room temperature. The DMF was removed in vacuo, ethyl acetate added and the solution washed with 5% aqueous citric acid, saturated brine, dried over anhydrous magnesium sulfate, filtered and concentrated to afford 109 mg of crude product. This was chromatographed on silica gel using 2.5% methanol/methylene chloride to afford 64 mg of pure product as a 1:1 mixture of diasteromers, m/e=532 (M+H).

Example 10

Preparation of t-butyl sulfamoylchoride

Part A:

A 25 mL two-necked RB flask, equipped with a reflux condenser and dropping funnel and under a nitrogen atmosphere, was charged with t-butanol (207 uL, 2.2 mmoles) and 5 mL of hexane. Chlorosulfonyl isocyanate (192 uL, 2.2 mmoles) in 3 mL of hexane is added dropwise. Upon warming a homogeneous solution is obtained. The solution is heated at gently reflux for 45 min., then is cooled to r.t. Solvent is removed under a steady stream of nitrogen. The crude t-butyl sulfamoyl chloride (a liquid) is used without further purification.

Example 11

Preparation of

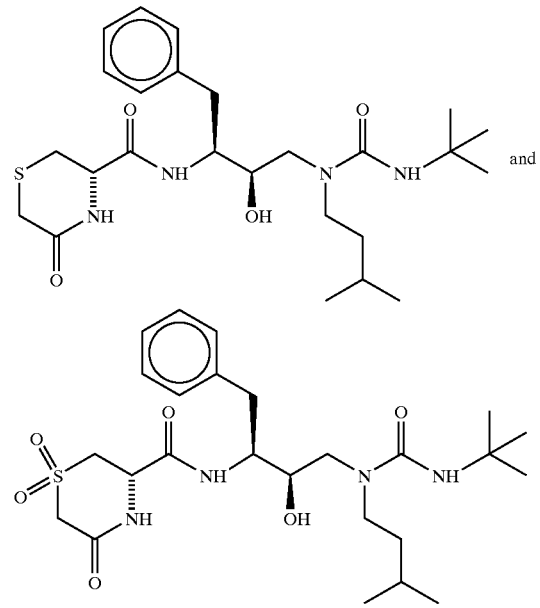

and

Part A: Preparation of 5-oxo-3-thiomorpholine-1(S)-carboxylic acid.

Part A: To a mixture of 4.0 g (22.8 mmol) of D-cysteine hydrochloride in 42 mL of methanol and 16 mL of water, was added 9.2 g (45.5 mmol) of triethylamine, followed by 2.46 g (22.8 mmol) of methyl chloroacetate. After 72 h at room temperature, the solvents were removed under reduced pressure and ethyl acetate added as well as concentrated hydrochloric acid. The layers were separated and the ethyl acetate, dried and concentrated to afford 203 mg of the desired product, m/e=162(M+H).

Part B: To a solution of 103 mg (0.64 mmol) of the cyclic sulfide from part A and 147 mg (0.96 mmol) N-hydroxybenzotriazole in 2 mL of anhydrous N,N-dimethylformamide (DMF) at 0° C., was added 135 mg (0.70 mmol) of EDC. After two hours, a solution of 202 mg (0.58 mmol) of amine in 2 mL of DMF from Example Part was added and the solution stirred at room temperature for 17 h. The solvents were removed in vacuo, ethyl acetate added and washed with saturated aqueous sodium bicarbonate, 5% aquious citric acid, and saturated sodium chloride, dried and concentrated to afford 230 mg of crude product. Chromatography on silica gel using 3–5% methanol/methylene chloride afforded 196 mg of the desired product, M/e=499 (M+Li), identified as 3-thiomorpholine- 1(S)-carboxamide, N-[3-[[[(1,1-dimethylethyl)amino]
carbonyl](3-methylbutyl)amino]-2(R)-hydroxy-1(S)-
(phenylmethyl)propyl]-5-oxo-carbonyl](3-methylbutyl)
amino]-2(R)-hydroxy-1(S)-(phenylmethyl)propyl]-5-oxo-.

Part C: To a solution of 151 mg (0.31 mmol) of the product of part B in 10 mL of chloroform was added 200 mg (0.78 mmol) of 67% m-chloroperbenzoic acid. After 16 h at room temperature, methylene chloride was added, the solution washed with 2 M aquious ammonium hydroxide, dried and concentrated to afford 150 mg of crude product. Chromatography on silica gel using 3–5% isopropanol/methylene chloride afforded 70 mg of the desired product, m/e=521 or 531 (M+Li), identified as 3-thiomorpholine-1(S)-carboxamide, N-[3-[[[(1,1-dimethylethyl)amino]carbonyl](3-methylbutyl)amino]-2(R)-hydroxy-1(S)-phenylmethylpropyl]-3,3,5-trioxo-.

Example 12

Preparation of

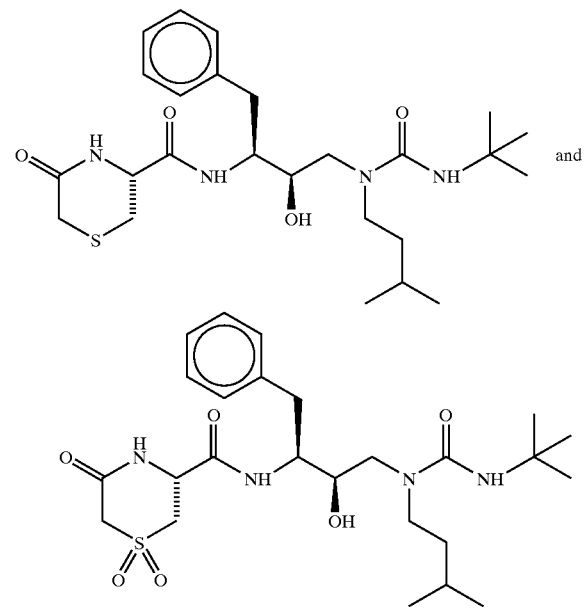

and

Part A: Preparation of 5-oxo-3-thiomorpholine-1(R)-carboxylic acid.

To a solution of 2.0 g (16.5 mmol) of L-cysteine in 30 mL of methanol and 10 mL of water, was added 3.33 g (33 mmol) of triethylamine and then 1.79 g (16.5 mmol) of methyl chloroacetate. After 21 h at room temperature, the solvents were removed in vacuo, saturated aqueous sodium bicarbonate was added and the solution extracted with ethyl acetate. The aquious layer was then acidified and extracted with ethyl acetate. The organic layer was dried and concentrated in vacuo. The residue was dried over $P_2O_5$ in vacuo, ethyl acetate added and the resulting solid collected by filtration to afford 306 mg of the desired product, m/e=161 (M+).

Part B: To a solution of 205 mg (1.27 mmol) of the cyclic sulfide from part A and 292 mg (1.91 mmol) of N-hydroxybenzotriazole in 5 mL of anhydrous N,N-dimethylformamide at 0° C. was added 268 mg (1.40 mmol) of EDC. After 2 h, a solution of 398 mg (1.14 mmol) of amine from Example, Part in 2 mL of DMF was added. After 17 h at room temperature, the solvent was removed in vacuo, ethyl acetate added, washed with saturated sodium becarbonate, 5% aquious citric acid, saturated soduim chloride, dried and concentrated to afford 448 mg of crude product. Chromatography on silica gel using 3–5% methanol/methylene chloride afforded 243 mg of the desired product, m/e=499 (M+Li), identified as 3-thiomorpholine-(1R)-carboxamide, N-[3-([[[(1,1-dimethylethyl)amino]carbonyl](3-methylbutyl)amino]-1(R)-hydroxy-1(S)-(phenylmethyl)propyl]-5-oxo-.

Part C: To a solution of 240 mg (0.49 mmol) of the product from Part B in 10 mL of chloroform was added 314 mg (1.22 mmol) of 67% m-chloroperbenzoic acid. After 17 h at room temperature, methylene chloride was added and washed with 2M aqueous ammonia, water, brine, dried and concentrated to afford 214 mg of crude material. Chromatography on silica gel using 5%–10% isopropanol/methylene chloride afforded 100 mg of the desired sulfone, m/e=531 or 521(M+Li), identified as 3-thiomorpholine-1(R)-carboxamide, N-[3-[[[(1,1-dimethylethyl)amino]carbonyl](3-methylbutyl)amino]-2(R)-hydroxy-1(S)-(phenylmethyl)propyl]-3,3,5-trioxo-.

Example 13

Preparation of 2H-Thiopyran-3-carboxamide, N-[3[[[(1,1-dimethylethyl)amino]carbonyl](3-methylbutyl)amino]-2(R)-hydroxy-1(S)-(phenylmethyl)propyl]-5,6-dihydro-, 1,1-dioxide

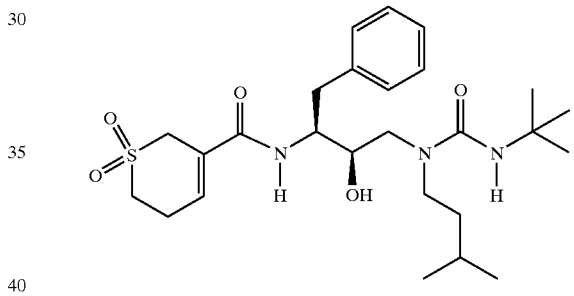

Part A: Preparation of 5,6-dihydro-2Hthiopyran-3-carboxylic acid, 1,1-dioxide.

To a solution of 205 mg (1.08 mmol) of methyl 5,6-dihydro-2H-thiopyran-3-carboxylate, 1,1-dioxide from Example 1 part D in 10 mL of 4N HCl/dioxane, was added 5 mL of water, After stirring at room temperature for 2 weeks, the solvents were removed in vacuo to provide a 65:35 mixture, respectively, of the desired acid and unreacted ester, respectively. The mixture was used directly in the next step.

Step B:

To a solution of 115 mg of the mixture from Part A, and 136 mg (0.89 mmol) N-hydroxybenzotriazole in 2 mL of anhydrous N,N-dimethylformamide (DMF) at 0° C., was added 136 mg (0.71 mmol) of EDC. After 2 hours at 0° C., a solution of 206 mg (0.59 mmol) of amine from Example 4, Part A, above, in 1 mL of DMF was added. After 16 hours at room temperature, ethyl acetate was added and washed with aqueous citric acid, water, brine, dried and concentrated to afford 219 mg of crude material. This was chromatographed on silica gel using 0.5–2% methanol/methylene chloride to afford 178 mg (60% yield) of the desired olefinic cyclic sulfone product, m/e 514 (M+Li).

Example 14
Preparation of Tetrahydrothiopyran-4-carboxamide, N-[3 [[[(4-methoxyphenyl)sulfonyl](3-methylbutyl)amino]-2R-hydroxy-15-(phenylmethyl}propyl]]-, 1,1-dioxide.

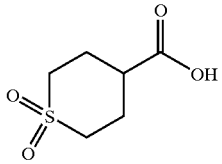

Preparation of tetrahydrothiopyran-4-carboxylic acid, 1,1-dioxide.

Part A: Preparation of Tetrahydrothiopyran-4-ol

To a solution of 6.36 g (54.7 mmol) of tetrahydropyran-4-one in 200 mL of anhydrous methanol at 0° C. under a nitrogen atmosphere, was added 1.04 g (27.4 mmol) of sodium borohydride. After 15 Minutes, 30 mL of water was added, the methanol was removed in vacuo and the resulting residue extracted twice with methylene chloride, dried and concentrated to afford 6.25 g (97% yield) of the desired alcohol, m/e=118 (M+).

Part B: Preparation of Tetrahydrothiopyran-4-ol, O-methanesulfonate.

To a solution of 6.25 g (53 mmol) of the alcohol from Part A in 50 mL of anhydrous methylene chloride and 12.9 mL (159 mmol) of pyridine at 0° C., was added dropwise 7.38 mL (95 mmol) of methanesulfonyl chloride and the solution allowed to stir at room temperature for sixteen hours. Ethyl acetate (200 mL) was added and the reaction mixture washed with 2N hydrochloric acid, saturated aqueous sodium bicarbonate, brine, dried and concentrated to afford 10.4 g of crude material. Chromatography on silica gel using 0.5% methanol/methylene chloride afforded 9.88 g (95% yield) of the desired mesylate, m/e=197 (M+H).

Part C: Preparation of Tetrahydrothiopyran-4-cyano

To a solution of 7.75 g (39.4 mmol) of the mesylate from Part B in 100 mL of anhydrous N-methylpyrrolidinone was added 19.3 g (395 mmol) of sodium cyanide. The mixture was heated at 90° C. for twenty hours, cooled, 200 mL of water added and the solution extracted three times with diethyl ether. The organic layer was dried and concentrated to afford 15.8 g of material which still contained N-methylpyrrolidinone. Chromatography on silica gel using 0.5% methanol/methylene chloride afforded a mixture of the desired nitrile, contaminated with the olefin resulting from elimination of the mesylate. Chromatography on silica gel using 10% ethyl acetate/hexane afforded 1.94 g (39% yield) of the desired nitrile, m/e=128 (M+H).

Part D: Preparation of Tetrahydrothiopyran-4-carboxamide.

To 3 mL of concentrated sulfuric acid, was added 813 mg (6.4 mmol) of the nitrile from Part C and the mixture heated at 45° C. for sixteen hours. The solution was cooled and poured into 50 mL of ice and water, the solids collected, dissolved in ethyl acetate, dried and concentrated to afford 614 mg (66% yield) of the desired amide, m/e=145 (M+).

Part E: Preparation of tetrahydrothiopyran-4-carboxylic Acid.

To a solution of 601 mg (4.1 mmol) of the amide from Part D in 10 mL of methanol was added 828 mg (21 mmol) of sodium hydroxide and the mixture heated at reflux for sixteen hours, 5 mL of water added and heating continued for 72 hours. The methanol was removed in vacuo, 2N hydrochloric acid added and the solution extracted with ethyl acetate, dried and concentrated to afford 571 mg (94% yield) of the desired acid, m/e=147 (CI,M+H).

Part F: Preparation of Tetrahydrothiopyran-4-carboxylic Acid, 1,1-dioxide.

To a solution of 200 mg (1.3 mmol) of the acid from Part E in 9 mL of acetic acid was added 620 mg (5.5 mmol) of 30% aqueous hydrogen peroxide. After heating at reflux for 1.5 hours, the colution was cooled, sodium sulfite added to quench any excess oxidizing agent (using potassium iodide/starch paper for detection), the volatiles removed in vacuo and the residue extracted with warm ethyl acetate, which was quickly filtered and concentrated to afford 140 mg (59% yield) of the desired sulfone, m/e=179 (M+H).

Tetrahydrothiopyran-4-carboxamide, N-[3-[[[(4-methoxyphenyl)sulfonyl] (3-methylbutyl)amino]-2R-hydroxy-18-(phenylmethyl)propyl]]-, 1,1-dioxide.

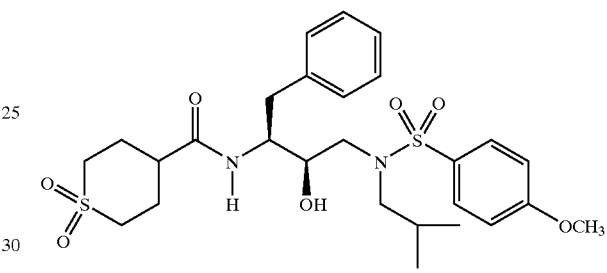

To a solution of 53 mg (1.1 mmol) of tetrahydrothiopyran-4-carboxylic acid, 1,1-dioxide and 62 mg (1.5 mmol) of N-hydroxybenzotriazole in 2 mL of anhydrous N,N-dimethylformamide (DMF) at 0° C., was added 62 mg (1.2 mmol) of EDC. After 2 hours at 0° C., a solution of 3-[[(4-methoxyphenyl)sulfonyl](2-methylpropyl)amino]-2R-hydroxy-3S-(phenylmethyl)propylamine in 1 mL of DMF was added. After sixteen hours at room temperature, the volatiles were removed in vacuo, ethyl acetate acid, washed with 5% aqueous citric acid, saturated sodium bicarbonate, brine, dried and concentrated to afford 142 mg of crude product. This was chromatographed on silica gel using 2.5% methanol/methylene chloride to afford 127 mg (83% yield) of the desired product, m/e=.

Example 15

Assays

Part A: Enzyme Assay

The compounds of the present invention are effective HIV protease inhibitors. Utilizing an enzyme assay as described below, the compounds set forth in Examples 4, 4a, 7, 8 and 9 inhibited the HIV enzyme in an amount described as an $IC_{50}$ ranging from about 3 nanomolar to about 140 nanomolar as shown in Table 1. The calculated $IC_{50}$ indicates the concentration providing inhibition of 50%, i.e., the concentration at which the inhibitor compound reduces enzyme activity by 50%). The enzyme method is described below. The substrate is 2-aminobenzoyl-Ile-Nle-Phe(p-$NO_2$)-Gln-Arg$NH_2$. The positive control is MVT-101 [Miller, M. et al, Science, 246, 1149 (1989)]. The assay conditions are as follows: Assay buffer: 20 mM sodium phosphate, pH 6.4

20% glycerol 1 mM EDTA 1 mM DTT 0.1% CHAPS

The above described substrate is dissolved in DMSO, then diluted 10 fold in assay buffer. Final substrate concentration in the assay is 80 IM.

HIV protease is diluted in the assay buffer to a final concentration of glycerol is 18%. The test compound is dissolved in DMSO and diluted in DMSO to 10× the test concentration; 10 IL of the enzyme preparation is added, the materials mixed and then the mixture is incubated at ambient temperature for 15 minutes. The enzyme reaction is initiated by the addition of 40IL of substrate. The increase in fluorescence is monitored at 4 time points (0, 8, 16 and 24 minutes) at ambient temperature. Each assay is carried out in duplicate wells.

TABLE 1

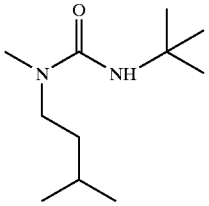

| Examples | Q | $IC_{50}$ | $EC_{50}$ | $TD_{50}$ |
|---|---|---|---|---|
| 4 | 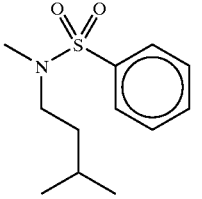 | 13 nM | 63 NM | 308,000 nM |
| 8 | 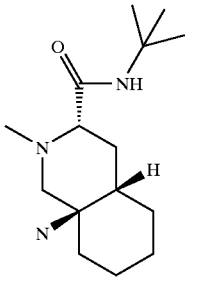 | 4 nM | 19 NM | 46,000 nM |
| 7 | 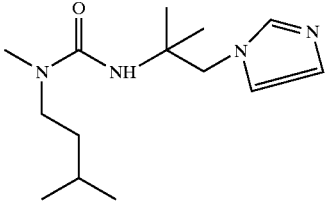 | 3 nM | 12 nM | 48,000 nM |
| 4a |  | 46 nM | 295 nM | 420,000 nM |

TABLE 1-continued

| Examples | Q | IC$_{50}$ | EC$_{50}$ | TD$_{50}$ |
|---|---|---|---|---|
| 9 | (structure with O=S(=O)(N-methyl, N-isobutyl)-NH-t-butyl) | 140 nM | — | — |

Thus, the compounds of the present invention are effective antiviral compounds and, in particular, are effective retroviral inhibitors as shown above. Thus, the subject compounds are effective HIV protease inhibitors. It is contemplated that the subject compounds will also inhibit other viruses such as human T-cell leukemia virus, respiratory syncitial virus, hepadnavirus, cytomegalovirus and picornavirus by the proposed inhibition of post translational proteolytic processing events. Thus, the subject compounds are effective in the treatment and/or prophylaxis of retroviral infections.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and other. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular made of administration.

The dosage regimen to give relief from or ameliorate a disease condition (i.e., treatment) or protecting against the further spreading of the infection (i.e., prophylaxis) with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The parental as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pill, powders, and granules. In such solid dosage forms, the active compound may be admixed with at least one inert diluent such as sucrose, lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Pharmaceutically acceptable carriers encompass all the foregoing and the like.

While the compounds of the invention can be administered as the sole active pharmaceutical agent, they can also be used in combination with one or more immunomodulators, antiviral agents or other antiinfective agents. For example, the compounds of the invention can be administered in combination with AZT or with N-butyl-1-deoxynojirimycin for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and condition.

What is claimed is:
1. A compound represented by the formula (I"):

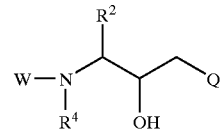

(I")

or a pharmaceutically acceptable salt, prodrug, or ester thereof wherein W represents

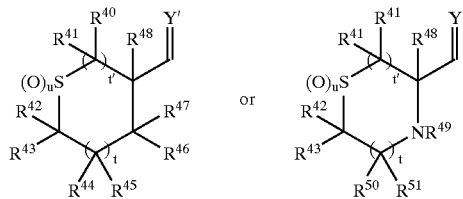

wherein
  Y' represents O, S, or $NR^{15}$, wherein $R^{15}$ represents a hydrogen radical or a radical as defined for $R^3$;
  t represents 0, 1, or 2;
  t' represents 1 or 2;
  u represents 0, 1, or 2;
  $R^{40}$, $R^{41}$, $R^{42}$, $R^{43}$, $R^{48}$, $R^{49}$, $R^{50}$, and $R^{51}$ independently represent a hydrogen radical or an alkyl radical;
  $R^{44}$, $R^{45}$, $R^{46}$, and $R^{47}$ independently represent a hydrogen radical, an alkyl radical, or a hydroxyl radical; or (a) $R^{40}$ together with $R^{48}$, (b) $R^{43}$ together with $R^{45}$, (c) $R^{45}$ together with $R^{47}$ or (d) $R^{47}$ together with $R^{48}$ represent a bond; or (a) $R^{44}$ together with $R^{45}$ and the carbon to which they are bonded, (b) $R^{46}$ together with $R^{47}$ and the carbon to which they are bonded or (c) $R^{50}$ together with $R^{51}$ and the carbon to which they are bonded represent a carbonyl radical;
  $R^6$ represents a hydrogen radical or an alkyl radical;
  $R^2$ represents a radical selected from the group consisting of alkyl, aryl, cycloalkyl, cycloalkyalkyl, and aralkyl, which radical is optionally substituted with a substituent selected from the group consisting of alkyl, $-NO^2$, $-CN$, $-CF^3$, $-OR^9$, $-SR^9$, and halogen, wherein $R^9$ represents a hydrogen radical or an alkyl radical;
  Q represents

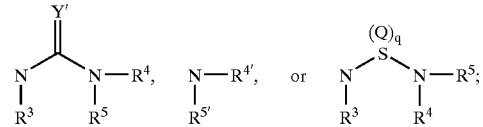

$R^3$ represents a radical selected from the group consisting of hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkyalkyl, aryl, aralkyl, heteroaralkyl, aminoalkyl, and mono- and disubstituted aminoalkyl, wherein said mono- and disubstituted aminoalkyl are substituted with one or two substituents, respectively, independently selected from the group consisting of alkyl, aryl, aralkyl, cycloalkyl, cycloalkylalkyl, heteroaryl, heteroaralkyl, heterocycloalkyl, and heterocycloalkylalkyl, or wherein said disubstituted aminoalkyl is substituted with two substituents that, together with the nitrogen atom to which they are bonded, form a radical selected from the group consisting of heterocycloalkyl, heteroaryl, thioalkyl, alkylthioalkyl, arylthioalkyl, and the sulfone or sulfoxide derivatives of thioalkyl, alkylthioalkyl, or arylthioalkyl;

$R^4$ and $R^5$ together with the nitrogen atom to which they are bonded represent a heterocycloalkyl radical or a heteroaryl radical;

$R^4$ and $R^5$ together with the nitrogen atom to which they are bonded represent an N-heterocyclic moiety;

q represents 1 or 2; and n represents 0, 1, 2, 3, 4, 5, or 6.

2. The compound of claim 1, wherein $R^4$ and $R^5$ together with the nitrogen atom to which they are bonded represent a heterocycloalkyl radical or a heteroaryl radical selected from the group consisting of pyrrolidinyl, piperidinyl, piperazinyl, morpholinyl, thiamorpholinyl, pyrrolyl, imidazolyl, pyrazolyl, pyridyl, pyrazinyl, pyrimidinyl, furyl, thienyl, triazolyl, oxazolyl, thiazolyl indolyl, quinolinyl, isoquinolmyl, tetrahydroquinolinyl, 1,2,3,4-tetrahydroisoquinolyl, quinoxalinyl, β-carbolinyl, 2-benzofunancarbonyl, and 1-, 2-, 4-, or 5-benzimidazolyl, wherein (a) when said heterocycloalkyl radical or a heteroaryl radical is piperazinyl, morpholinyl, thiamorpholinyl, imidazolyl, pyridyl, pyrazinyl, pyrimidinyl, quinolyl, isoquinolyl, tetrahydroisoquinolyl, quinoxalinyl, or benzimidazolyl, it is optionally substituted on a secondary nitrogen atom by alkyl, aralkoxycarbonyl, alkanoyl, phenyl, or phenylalkyl and (b) when said heterocycloalkyl radical or a heteroaryl radical is pyrrolidmyl, piperidinyl, piperazinyl, pyrrolyl, pyrazolyl, pyrazinyl, pyrmudinyl, triazolyl, oxazolyl, thiazolyl, indolyl, tetrahydroquinolyl, quinoxalinyl, or benziniidazolyl, it is optionally substituted on one or more tertiary nitrogen atoms by oxido.

3. The compound of claim 2, wherein $R^4$ and $R^5$ together with the nitrogen atom to which they are bonded represent a heterocycloalkyl radical or a hetetoaryl radical selected from the group consisting of pyrrolidinyl, piperidinyl, piperazinyl, morpholinyl, thiamorpholinyl, pyrrolyl, imidazolyl, pyrazolyl, triazolyl, indolyl, tetrahydroquinolinyl, β-carbolinyl, and 1-, 2-, 4-, or 5-benzimidazolyl.

4. The compound of claim 3, wherein $R^4$ and $R^5$ together with the nitrogen atom to which they are bonded represent an N-heterocyclic moiety selected from the group consisting of pyrrolidinyl, piperidinyl, piperazinyl, morpholinyl, thiamorpholinyl, tetrahydroquinolinyl, β-carbolinyl, and 1-, 2-, 4-, or 5-benziniidazolyl.

5. The compound of claim 1, wherein $R^{4'}$ and $R^{5'}$ together with the nitrogen atom to which they are bonded represent an N-heterocyclic moiety selected from the group consisting of

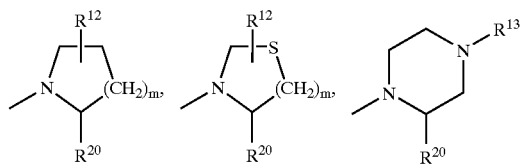

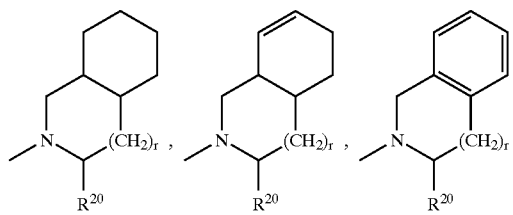

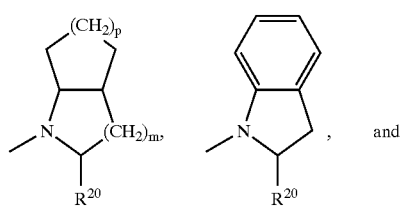

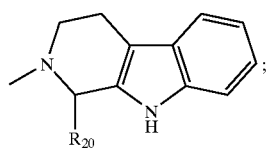

wherein $R^{12}$ represents a radical selected from the group consisting of hydrogen, hydroxyl, alkoxycarbonylamino and acylamino;

$R^{13}$ represents a radical selected from the group consisting of hydrogen, alkyl, aryl, alkoxycarbonyl and acyl;

m represents 1, 2, 3, or 4;

p represents 1 or 2;

r represents 0, 1, or 2; and $R^{20}$ represents a radical selected from the group consisting of hydrogen, alkyl, aikoxycarbonyl, monoalkylcarbamoyl, monoalkylcarbamoyl, monoarylcarbamoyl, and

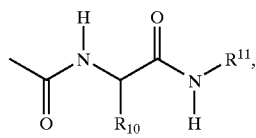

wherein $R^{10}$ and $R^{11}$ each independently represent an alkyl radical.

6. The compound of claim 1, represented by the formula (I')

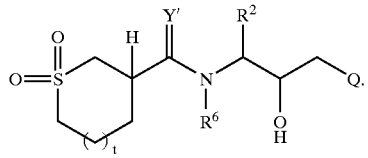

(I')

7. The compound of claim 6, wherein t represents 1, $R^6$ represents a hydrogen radical, and $R^2$ represents a radical selected from the group consisting of aralkyl, alkyl, and cycloalkyl.

8. The compound of claim 6, wherein Q represents

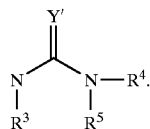

9. The compound of claim 8, wherein t represents 1, $R^6$ represents a hydrogen radical, and Y' represents O.

10. The compound of claim 8, wherein $R^2$ represents a radical selected from the group consisting of benzyl, cyclohexylmethyl, n-butyl, 2-naphthylmethyl, p-fluorobenzyl, and isobutyl.

11. The compound of claim 8, wherein $R^3$ represents a radical selected from the group consisting of isobutyl, n-butyl, isoamyl, benzyl, p-fluorobenzyl, and cyclohexylmethyl.

12. The compound of claim 6, wherein Q represents

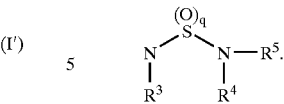

13. The compound of claim 12, wherein t represents 1, $R^6$ represents a hydrogen radical, Y' represents O, and q represents 2.

14. The compound of claim 12, wherein $R^2$ represents a radical selected from the group consisting of benzyl, p-fluorobenzyl, 2-naphthylmethyl, n-butyl, cyclohexylmethyl, and isobutyl.

15. The compound of claim 1, wherein $R^3$ represents a radical selected from the group consisting of isobutyl, n-propyl, n-butyl, isoamyl, benzyl, cyclohexylmethyl, and cyclohexyl.

16. The compound of claim 1, wherein the carbon atom bearing the hydroxyl group and adjacent to the carbon atom bearing $R^2$ has a stereochemistry designated as (R).

17. A pharmaceutical composition comprising a retroviral protease inhibitory effective amount of the compound of claim 1 and a pharmaceutically acceptable carrier.

18. A method for treating a retroviral infection, said method comprising administering the composition of claim 17.

19. The method of claim 18, wherein said retroviral infection is an HIV infection.

20. A method for inhibiting a retroviral protease, said method comprising administering a retroviral protease inhibitory effective amount of the compound of claim 1.

* * * * *

UNITED STATES PATENT AND TRADEMARK OFFICE
CERTIFICATE OF CORRECTION

PATENT NO. : 6,875,790 B2  
DATED : April 5, 2005  
INVENTOR(S) : Deborah E. Bertenshaw et al.

It is certified that error appears in the above-identified patent and that said Letters Patent is hereby corrected as shown below:

Title page,  
Item [*] Notice, insert -- This patent is subject to a Terminal Disclaimer --.

Column 50,  
Line 57, replace "—$NO^2$," with -- —$No_2$, --.  
Line 58, replace "—$CF^3$," with -- —$CF_3$, --.

Column 51,  
Line 15, replace "$R^4$ and $R^5$" with -- $R^{4'}$ and $R^{5'}$ --.  
Line 44, replace "benziniidazolyl," with -- benzimidazolyl --.  
Line 62, replace "5-benziniidazolyl." with -- 5-benzimidazolyl. --.

Column 52,  
Line 54, replace "aikoxycarbonyl," with -- alkoxycarbonyl, --.

Signed and Sealed this

Twenty-first Day of March, 2006

JON W. DUDAS  
*Director of the United States Patent and Trademark Office*